US009321849B2

(12) United States Patent
Vita et al.

(10) Patent No.: US 9,321,849 B2
(45) Date of Patent: Apr. 26, 2016

(54) URANIUM-CHELATING PEPTIDES AND USES THEREOF

(75) Inventors: Claudio Vita, Gif sur Yvette (FR); Mireille Sauvage-Vita, legal representative, Gif sur Yvette (FR); Fabio Vita, legal representative, Gif sur Yvette (FR); Elena Vita, legal representative, Gif sur Yvette (FR); Loïc Le Clainche, Paris (FR); Véronique Monjardet, Paris (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 1106 days.

(21) Appl. No.: 12/979,787

(22) Filed: Dec. 28, 2010

(65) Prior Publication Data

US 2011/0093964 A1 Apr. 21, 2011

Related U.S. Application Data

(62) Division of application No. 10/562,323, filed as application No. PCT/FR2004/001698 on Jul. 1, 2004, now Pat. No. 7,888,311.

(30) Foreign Application Priority Data

Jul. 4, 2003 (FR) ..................................... 03 08211

(51) Int. Cl.
*A61K 38/16* (2006.01)
*C07K 14/00* (2006.01)
*C01G 43/00* (2006.01)
*C07K 19/00* (2006.01)
*C07K 14/47* (2006.01)
*A61K 38/00* (2006.01)

(52) U.S. Cl.
CPC ............. *C07K 19/00* (2013.01); *C07K 14/4728* (2013.01); *A61K 38/00* (2013.01); *C07K 2319/00* (2013.01); *G01N 2333/4727* (2013.01)

(58) Field of Classification Search
None
See application file for complete search history.

(56) References Cited

PUBLICATIONS

Le Clainche et al., "Engineering new metal specificity in EF-hand peptides," JBIC Journal of Biological Inorganic Chemistry, vol. 8, No. 3, Nov. 20, 2002, pp. 334-340.
Fischer et al., "Multiple Devergent MRNAs Code for a Single Human Calmodulin", Journal of Biological Chemistry, American Society of Biological Chemists, vol. 263, No. 32, Nov. 15, 1988, pp. 17055-17062.

Procyshyn et al., "A structure/activity study of calcium affinity and selectivity using a synthetic peptide model of the helix-loop calcium-binding motif", Journal of Biological Chemical, vol. 269, No. 3, 1994, pp. 1641-1647.
Marsden et al., "Calcium Binding Proteins Elucidating the Contributions to Calcium Affinity from an Analysis of Species Variants and Peptide Fragments", Biochemistry and Cell Biology, vol. 68, No. 3, 1990, pp. 587-601.
Bender et al., "The Abundance of Calmodulin Messenger RNA is Regulated in Phosphorylase-Kinase Deficient Skeletal Muscle", Journal of Biological Chemistry, vol. 263, No. 20, 1988, pp. 9733-9737.
Rhyner et al., "Structure of the Human Calm1 Calmodulin Gene and Identificaiton of Two Calm1-Related Pseudogenes Calm1P1 and Calm1P2", European Journal of Biochemistry, vol. 225, 1994, pp. 71-82.
Buchta et al., "Peptides Related to the Calcium Binding Domains II and III of Calmodulin Synthesis and Calmodulin-Like Features", International Journal of Peptide and Protein Research, vol. 28, No. 3, 1986, pp. 289-297.
Babu et al., "Structure of Calmodulin Refined at 2.2 A Resolution" Journal of Molecular Biology, vol. 204, No. 1, 1988, pp. 191-204.
Wilson et al., "The 1.0 A crystal structure of Ca<2+>-bound calmodulin: an analysis of disorder and implications for functionally relevant plasticity", Journal of Molecular Biology, vol. 301, No. 5, Sep. 1, 2000, pp. 1237-1256.
Reid, R.E., "Synthetic Fragments of Calmodulin Calcium-Binding Site III a Test of the Acid Pair Hypothesis", Journal of Biological Chemistry, vol. 265, No. 11, 1990, pp. 5971-5976.
"The EF-hand Calcium-binding Proteins Data Library", Online at http://structbio.vanderbilt.edu/cabp_database/, Jan. 17, 2005.
McCormack et al., "Calmodulins and related potential calcium sensors of Arabidopsis", New Phytologist, vol. 159, No. 3, Sep. 2003, pp. 585-598.
Bertini et al., "Tuning the affinity for lanthanides of calcium binding proteins", Biochemistry, vol. 42, No. 26, pp. 8011-8021.
Bhattacharya et al., "Target selectivity in EF-hand calcium binding proteins", Biochimica Et Biophysica Acta., Dec. 6, 2004, Vo. 1742, No. 1-3, pp. 69-79.
Finn et al., "The evolving model of calmodulin structure, function and activation", Structure, Current Biology Ltd., vol. 3, No. 1, Jan. 1995, pp. 7-11.

(Continued)

*Primary Examiner* — Satyanarayana R Gudibande
(74) *Attorney, Agent, or Firm* — Alston & Bird LLP

(57) ABSTRACT

The invention concerns uranium-chelating peptides as well as their uses for decontaminating soils and water, and for detecting and treating people contaminated by uranium. Said peptides have a helix-loop-helix type structure comprising the sequence of a calmodulin loop including at least one mutation of neutral residues selected from the group consisting of S, T, C, H, Y, N and Q, of one, two or three residues of at least one of the four calmodulin calcium binding sites: site I: residues selected among D20, D22 and D24 residues; site II: residues selected among D56, D58 and N60 residues; site III: residues selected among D93, D95 and N97 residues; site IV: residues selected among D129, D131 and D133 residues; said positions being indicated with reference to the human calmodulin sequence.

16 Claims, 17 Drawing Sheets

(56) References Cited

PUBLICATIONS

Nelson et al., "Structures of EF-hand Ca2+-binding proteins: Diversity in the organization, packing and response to Ca2+ binding", Biometals, vol. 11, No. 4, Dec. 1998, pp. 297-318.

Reid et al., "Engineering magnesium selectivity in the helix-loop-helix calcium-binding motif", Archives of Biochemistry and Biophysics, vol. 323, No. 1, 1995, pp. 115-119.

Database Swissprot 'en ligne! Mar. 15, 2004, "Calmodulin".

Babu et al., "Structure of Calmodulin Refined at 2.2 A Resolution", Journal of Molecular Biology, vol. 204, No. 1, 1988, pp. 191-204.

```
position   7                                        39
CaM   :    EQIAEFKEAFALFDKDGDGTITTKELGTVMRSL (SEQ ID NO :1)
CaM-M1c:   EQIAEFKEAFALCDKDGDGYITTKELGTCMRSL (SEQ ID NO :2)
CaM-M2c:   EQIAEFKEAFALCDKDGDGYITTKDLGTCMRSL (SEQ ID NO :3)
CaM-M3c:   EQIAEFKEAFALCTKTGDGYITTKELGTCMRSL (SEQ ID NO :4)
CaM-M4c:   EQIAEFKEAFALCNKNGNGYITTKELGTCMRSL (SEQ ID NO :5)
CaM-M5c:   EQIAEFKEAFALCDKTGTGYITTKELGTCMRSL (SEQ ID NO :6)
CaM-M6c:   EQIAEFKEAFALCTKTGDGYITTKELGTCMRSL (SEQ ID NO :7)
CaM-M7c:   EQIAEFKEAFALCSKDGSGYITTKELGTCMRSL (SEQ ID NO :9)
CaM-M8c:   EQIAEFKEAFALCTKTGTGYITTKELGTCMRSL (SEQ ID NO :10)
CaM-M9c    EQIAEFKEAFALCTKDGDGYITTKELGTCMRSL (SEQ ID NO :11)
CaM-M10c   EQIAEFKEAFALCDKDGTGYITTKELGTCMRSL (SEQ ID NO :12)
```

Figure 2

URANIUM-CHELATING PEPTIDES AND USES THEREOF

CROSS-REFERENCE TO RELATED APPLICATIONS

This application is a divisional of U.S. application Ser. No. 10/562,323, filed Oct. 17, 2007, now U.S. Pat. No. 7,888,331, which was a national stage filing under 25 U.S.C. 371 of International Application No. PCT/FR2004/001698, filed Jul. 1, 2004.

FIELD OF THE INVENTION

The present invention relates to uranium-chelating peptides and to uses thereof for decontaminating soils and water, and for detecting and treating individuals contaminated with uranium.

BACKGROUND

Uranium is normally present in the environment at a very low concentration, in the form of isotopes 238 (99.27%) and 235 (0.72%), which break down through the emission of alpha-particles of weak radiological toxicity; the uranyl form ($UO_2^{2+}$) represents the most common form of uranium in an oxygenated atmosphere.

However, in specific sites, for instance close to uranium mineral mines, storage sites (nuclear control or storage of uranium-depleted munitions) or else in the case of a nuclear accident, the concentration of this metal may be much higher and represents a danger for humans due to the fact that it accumulates in the kidneys and in the bones: toxicity for renal tissue and development of bone tissue cancers.

The decontamination of contaminated sites and individuals requires having, firstly, means for neutralizing the toxicity of the uranium in the environment and in the body of the contaminated individuals and, secondly, detection reagents that are effective and specific for this metal. However, no effective means for detecting and decontaminating uranium currently exists, in particular due to the absence of uranium-specific ligands capable of detecting uranium (sensor) and of chelating this toxic metal which could be present in an environment and/or in a biological medium that is contaminated, in order to perform the decontamination thereof.

The current treatment for decontaminating soils is carried out mainly by excavation, harvest and storage in appropriate sites or by extraction of the uranium using chelating agents; these physicochemical treatments are expensive, not very specific or not specific at all, and not very suitable for the treatment of very widespread contaminating surfaces, and also present a high risk of contamination for the operators, due to repeated exposure to uranium. Alternatively, it has been proposed to use living organisms (higher plants or microorganisms) for decontaminating soils and water contaminated with uranium. This method is based on absorption of the metals and therefore on their sequestration by these organisms. For example, plants are capable of absorbing toxic metals by the roots and of accumulating them in the leaves, which are subsequently harvested and stored in appropriate sites; the organisms currently available do not allow effective decontamination of contaminated soils and water because of their low capacity for extraction, tolerance and accumulation of high concentrations of toxic metals.

The detection of uranium in individuals who may have been contaminated with uranium is carried out ex situ by plasma mass spectrometry (ICP-MS); this technique is laborious to carry out and expensive.

The treatment of individuals contaminated with uranium is carried out by the administration of chelating agents which bind the uranium, thus promoting its excretion and consequently reducing its deposition in the kidneys and the bones. Among the main uranium-chelating agents, mention may be made of: diethylene-triaminepentacetic acid (DTPA), 5-aminosalicylic acid (5-AS), gallic acid, sulfocatechol, carboxycatechol and hydroxypyridinone; these chelating agents have the drawback of not being uranium-specific.

Various approaches have been developed for specifically detecting certain metals, in particular in an aqueous medium or in biological samples:

- fluorescent chemosensors (Tsien, 1993: *Fluorescent chemosensors for ion and molecule recognition*, pages 130-146, Czarnik A W (ed), American Chemical Society, Washington D.C.); these fluorescent sensors are specific for sodium, potassium, calcium and magnesium; on the other hand, no uranium-specific chemosensor has been described;
- fluorescent peptide sensors (biosensors) consisting of a peptide of approximately 26 amino acids, derived from a zinc finger domain, labeled with at least one fluorescent group (Walkup et al., 1996, J. Am. Soc., 119, 3443-3450; Godwin et al., 1998, J. Am. Soc., 118, 6514-6515; Walkup et al., 1997, J. Am. Soc., 119, 3443-3540). In the presence of zinc ions, these peptide biosensors form a structure around the metal and expose the fluorescent group to environmental changes that result in a variation in fluorescence emission that depends on the concentration of the metal. Alternatively, when the peptides are conjugated to two appropriate fluorescent groups, the binding of the zinc to the peptide results in a conformational modification favorable to an effective transfer of energy between the two fluorophores (Fluorescence Resonance Energy Transfer or FRET), resulting in the emission of a fluorescent signal proportional to the concentration of the metal (Walkup et al., 1996, mentioned above). Because of the structure of the "zinc finger" domain, which is suited to the chelation of ions with a tetrahedral geometry, like zinc, these biosensors do not make it possible to chelate uranium, which, in its uranyl form ($UO_2^{2+}$) which is the most common in an oxygenated medium, exhibits a pentagonal or hexagonal bipyramidal geometry with a coordination number of 7-8 (uranium VI);
- fluorescent protein sensors, called "chameleons", consisting of a fusion protein comprising successively, from its $NH_2$ end to its COOH end: a blue or cyan mutant (EBFP or ECFP, fluorescence donor) of the GFP fluorescent protein derived from the jellyfish *Aequorea victoria*, calmodulin (CaM) comprising the N- and C-terminal domains and calcium ion-binding sites I and II, a calmodulin-binding peptide of 26 residues that is derived from the calmodulin-binding domain of a myosin light chain kinase (MLCK), and another green or yellow mutant of the same fluorescent protein (EGFP or EYFP, fluorescence acceptor) (Miyawaki et al., Nature, 1997, 388, 882-887). The binding of calcium to calmodulin causes a conformational change in the fusion protein, which forms a new site to which the peptide binds, and which produces an association between the two fluorescent proteins and a positioning in the space that is favorable to effective energy transfer from the fluorescence donor (EBFP or ECFP) to the fluorescence acceptor (EGFP or EYFP), thus producing an increase in the fluorescence emitted by the fluorescence acceptor (EGFP or EYFP). Other "chameleon" fluorescent indicators that are more sensitive and specific for a broader range of calcium concentrations have also been obtained (Truong et al., *Nature Struct. Biol.*, 2001, 8, 1069-1073). This fluorescent indicator system, that is based on the conformational variations induced by the binding of calcium to the calmodulin-MLCKp complex, is calcium-specific and does not therefore make it possible to detect other metal ions, for instance uranyl;

peptide ligands selective for heavy metals, derived from helix-loop-helix motifs (Borin et al., Biopolymer, 1989, 28, 353-369; Dadlez et al., FEBS Lett., 1991, 282, 143, 146; Marsden et al., Biochem. Cell. Biol., 1990, 68, 587-601; Shaw et al., Science, 1990, 249, 280-283; Reid et al., Arch. Biochem. Biophys., 1995, 323, 115-119; Procyshyn et al., J. Biol. Chem., 1994, 269, 1641-1647); these peptides exhibit poor structuring of their helices in aqueous media, and also low affinities for divalent metals (Kd of the order of a millimolar);

bacteria containing a promoter that can reflect the presence of a toxic metal as a light signal (Bechor et al., Biotechnol., 2002, 94, 125-132; Lee et al., Biosen. Bioelectron., 2003, 18, 571-577); in these systems, the toxic agent acts as a cellular stress factor and thus induces an altered expression of a bioluminescent protein, which represents the detected signal; these systems are not therefore specific for uranium and for toxic metals in general.

It emerges from the above that uranium-specific ligands capable of detecting (sensor) and of chelating this toxic metal which could be present in an environment or in a biological medium that is contaminated, in order to carry out the decontamination thereof, currently do not exist. The specific chelation of uranium in the environment (soil, water, etc.) and in living organisms is nevertheless difficult to carry out, due to the presence of a large excess of other metals, such as alkaline earth metals or lanthanides which are competitors for uranium-binding.

Consequently, the inventors have given themselves the aim of providing an agent capable of specifically chelating uranium (VI), in the uranyl form ($UO_2^{2+}$)

SUMMARY

Calmodulin, which has a mass of 16.7 kDa, is ubiquitous in eukaryotic cells and plays an important role in the signal translation between various cellular compartments mediated by variations in calcium concentration. In response to an increase in the intracellular calcium concentration, it undergoes a conformational change that allows it to bind to and activate various cellular protein targets. This structural change is similar to that which is observed for troponin C and is essential in muscle contraction. The X-ray structure has been resolved and shows that the protein has two N- and C-terminal domains, each comprising two calcium ion-binding sites of the helix-loop-helix type, the structural motif most common for chelating calcium, present in many other calcium-binding proteins such as, for example, troponin C and parvalbumin. The structure of this motif is highly conserved in all proteins: a loop of 12 amino acids is framed by two alpha-helices; the loop coordinates the metal via aspartic acid and glutamic acid residues, and also by means of a carbonyl group of the peptide backbone and by means of a water molecule. The detailed structure of *Paramecium tetraurelia* calmodulin site I (FIG. 1) shows that the calcium is in a pentagonal bipyramidal geometry; the Ca—O distances are between 2.1 and 2.3 Å and the dissociation constants are of the order of 10 μM for the low-affinity sites I and II, and 1 μM for the high-affinity sites III and IV. Cooperation between these sites has been demonstrated: calcium binding to sites I and II greatly increases the affinity of sites III and IV. The sequence of the chelating loop is very conserved in calmodulin. In fact, humans and most vertebrates have the same sequence in this loop.

Based on the sequence of the helix-loop-helix motif of the calcium-binding sites of *Paramecium tetraurelia* calmodulin, the inventors have prepared mutant peptides that have the following properties:

they exhibit—in the form of an isolated peptide and in the presence of certain metals—an ordered conformation compatible with a helix-loop-helix structure, and they selectively bind—in the form of an isolated peptide or of a protein that includes at least one sequence of said peptide—uranium in its uranyl form with a high affinity (Kd of the order of 1 μM), even in the presence of other metals, of varied buffers or of other physiological or natural ions having coordination characteristics similar to those of uranium.

Such peptides or the proteins that include one or more of these peptide sequences have uses in:

the production of modified novel bacteria and novel plant species expressing proteins enriched in this peptide sequence, having an increased capacity for the binding, absorption and accumulation of this toxic metal, that are useful for the biological decontamination of soils and fluids contaminated with uranium, the manufacture of novel fluorescent peptide and protein sensors for uranium, that are useful for the specific detection of uranium, in particular in individuals who may be contaminated, the production of novel modified microorganisms that use the uranium-specific peptide or the calmodulin protein, including from one to four uranium-selective sites, as a sensitive element for reflecting the presence of uranium as a light signal, and the formulation of novel medicinal products for the treatment of individuals contaminated with uranium.

Consequently, a subject of the present invention is a peptide, characterized in that it has a helix-loop-helix type structure comprising the sequence of a calmodulin loop including at least one mutation to neutral residues selected from the group consisting of Ser (S), Thr (T), Cys (C), His (H), Tyr (Y), Asn (N) and Gln (O), of one, two or three residues of at least one of the four calcium-binding sites of calmodulin:

site I: residues selected from residues D20, D22 and D24,
site II: residues selected from residues D56, D58 and N60,
site III: residues selected from residues D93, D95 and N97,
site IV: residues selected from residues D129, D131 and D133, said positions being indicated with reference to the human calmodulin sequence (SWISSPROT P02593).

According to an advantageous embodiment of said peptide, the mutation is preferably a mutation to threonine (Thr), serine (Ser) or asparagine (Asn) neutral residues.

According to an advantageous arrangement of this embodiment, the mutation is preferably a mutation, to a threonine residue, of residue D20, D22 or D24, a mutation, to a threonine, serine or asparagine residue, of the two residues D20 and D24, of the two residues D20 and D22 or of the two residues D22 and D24, or a mutation, to a threonine, serine or asparagine residue, of the three residues D20, D22 and D24.

In accordance with the invention, in order to obtain a coordination complex in which the uranyl has a coordination number of 7 (pentagonal or hexagonal bipyramidal geometry), so as to provide the uranyl with, in addition to the two oxygen atoms in the apical position, 5 or 6 coordinating atoms placed at the four apexes of the "square base" of the bipyramid, the peptide according to the invention is modified compared with the corresponding natural peptide such that the number of carboxylic acid residues present in the loop (D20, D22 and D24, E31) is decreased in such a way that it is less than 4, by substituting at least one residue 24 or two of the other residues with one or two neutral residues.

Unless otherwise indicated, the positions of the mutations are indicated with reference to the human calmodulin sequence (SWISSPROT P02593).

The invention encompasses the peptides derived from the sequence of any vertebrate or invertebrate calmodulin.

For the purpose of the present invention, said loop is that of one of the calcium-binding sites of calmodulin (site I, II, III or IV), defined by the 12-amino acid sequence located from positions 20 to 31 (site I), 56 to 67 (site II), 93 to 104 (site III) and 129 to 140 (site IV), with reference to the human sequence (SWISSPROT P02593).

The peptide according to the invention consists of a calcium-binding site mutant comprising at least one mutation in the loop of the helix-loop-helix motif. Said calcium-binding site is either one of the calmodulin sites, or a hybrid site in which the loop is that of one of the calmodulin sites and the helices are those of another protein having a helix-loop-helix type motif, capable of binding calcium.

Consequently, the peptide having a helix-loop-helix type structure according to the present invention derives completely or partially from calmodulin.

When said peptide derives completely from calmodulin, it comprises the sequences of the helices adjacent to said loops which are present in calcium-binding sites I, II, III and IV, namely the sequences corresponding to those located, respectively, at positions 7 to 19 and 29 to 38 (site I), 45-55 and 65-78 (site II), 79-92 and 102-111 (site III), and 118-128 and 138-147 (site IV), with reference to the human sequence (SWISSPROT P02593).

Alternatively, when said peptide derives partially from calmodulin, it comprises the sequences of the helices of a protein having a helix-loop-helix type motif, capable of binding calcium, for instance troponin C, parvalbumin, calbindin, recoverin, neuro-calcin, calpain, oncomodulin, or the sarcoplasmic calcium-binding protein, members of the S100 protein and V1S protein family and the calcium-binding domains of myosin.

According to another advantageous embodiment of said peptide, it is a cyclic peptide which has helices that each include a mutation of an amino acid residue to a cysteine residue, which cysteines are connected via a disulfide bridge, or other residues allowing chemical bridging. Preferably, said peptide derives completely from calmodulin site I and has the mutations F19C and V35C; cyclic peptides having such mutations, and after binding of certain metals, advantageously exhibit an ordered structure of helix-loop-helix type when they are in the form of isolated peptides.

Alternatively, other modifications that involve a covalent or even noncovalent bond can stabilize the helix-loop-helix motif and replace the disulfide bridge.

According to another advantageous embodiment of said peptide, it also includes the mutation of a residue—different from the mutated residue(s) as defined above—to a fluorescent amino acid residue sensitive to the variations in the chemical environment induced by binding of the uranyl; preferably, said residue may be located in the loop or in the helices at a distance of less than 20 Å from the uranyl-binding site. Said fluorescent amino acid is advantageously a tyrosine residue (Y) or a tryptophan residue (W), and in particular the following residues: T26Y, T26W, A15W or F16W.

According to an advantageous arrangement of the above embodiments, said peptide is a mutant of calmodulin site I defined by one of the following sequences: SEQ ID Nos. 4-7 or SEQ ID Nos. 9-12; the mutations of these peptides are illustrated in table I.

According to yet another advantageous embodiment of said peptide, it is conjugated to at least one appropriate fluorophore, such as dansyl, coumarin, fluorescein and Alexa derivatives, at an appropriate amino acid residue, for example at positions 15 and 16 that are sensitive to the conformational variations and the variations in the chemical environment that are induced by binding of the uranyl to said fluorophore-labeled peptide.

According to another advantageous embodiment of said peptide, it is coupled to two different fluorophores, respectively a fluorescence donor and a fluorescence acceptor, at positions that induce conformational variations favorable to an energy transfer from the fluorescence donor to the fluorescence acceptor (fluorophores brought closer together), when the uranyl binds to said peptide labeled with two fluorophores.

Among fluorophores, use may be made of fluorescent proteins, in particular GFP and its mutants (EBFP, ECFP, EYFP, EGFP), and other fluorescent molecules derived from marine organisms, for instance DsRed, a red fluorescent protein of the tropical coral *Dixosoma* (Bowen B. et al., Photochem. Photobiol., 2003, 77, 4, 362-369), CopGFP, a green fluorescent protein (green monomeric GFP-like protein), distributed in particular by Evrogen, or PhiYFP, a yellow fluorescent protein distributed in particular by Evrogen.

According to yet another advantageous embodiment of said peptide, it is associated, by any appropriate means, with molecules that allow targeting to the kidney and/or to the bones, for example specific scFv molecules, specific growth factors or specific peptides.

According to yet another advantageous embodiment of said peptide, it is associated, by any appropriate means, with molecules that promote its excretion in vivo, for example with polyethylene glycol molecules.

A subject of the present invention is also a polypeptide, characterized in that it comprises the concatenation of at least two identical or different peptides as defined above.

Such polypeptides increase the affinity for uranium, due to the cooperation between various binding sites.

A subject of the present invention is also a peptide composition, characterized in that it comprises a polypeptide as defined above, comprising the concatenation of at least two identical or different peptides as defined above, associated with one another by any appropriate means, and at least one suitable vehicle.

A subject of the present invention is also a fusion protein, characterized in that it consists of the in-frame fusion of the sequence of at least one peptide as defined above, with the sequence of an appropriate protein.

In accordance with the invention, said peptide is fused at a permissive site of said protein, i.e. at a region of this protein which, when it is fused to the sequence of at least one peptide according to the invention, confers on said fusion protein an affinity and a specificity for uranium VI, of the order of that of the isolated peptide.

Among appropriate proteins, mention may be made of proteins having a helix-loop-helix motif, capable of binding calcium, in particular calmodulin and proteins derived from the latter proteins, in particular the "chameleon" sensors, according to the principle as described in Miyaki et al. and Truong et al., mentioned above.

For example, when said protein is calmodulin or a chameleon protein derived from the latter, the sequence of said peptide is inserted instead and in place of the corresponding sequence in calmodulin, i.e. in place of the native loop (nonmutated) or the native helix-loop-helix motif (nonmutated).

According to an advantageous embodiment of said fusion protein, it is conjugated, by any appropriate means, to at least one fluorophore as defined above. Preferably, one of the ends of said protein is coupled to a fluorescence donor and the other end is coupled to a fluorescence acceptor. Preferably, said protein comprises, at one of its ends, the sequence of EBFP or ECFP and, at the other end, the sequence of EGFP or of EYFP.

The fluorescent peptides, polypeptides and proteins as defined above which exhibit a high affinity and a specificity for uranium, represent fluorescence sensors specific for uranium VI that are useful for detecting and assaying uranium in contaminated soils and water, and also in an appropriate biological sample, in particular a body fluid sample, derived from an individual who may be contaminated with uranium.

Consequently, a subject of the present invention is also the use of a peptide, of a polypeptide or of a fusion protein, as defined above, or a peptide selected from the group consisting of the peptides having a helix-loop-helix type structure of a protein capable of binding calcium, as defined above, for preparing a reagent for detecting soils and water contaminated with uranium, and also for diagnosing individuals contaminated with uranium. Preferably, said peptides and said fusion proteins are conjugated to at least one fluorophore, as defined above.

A subject of the present invention is also the use of a peptide, of a polypeptide or of a fusion protein, as defined above, or a peptide selected from the group consisting of the peptides having a helix-loop-helix type structure of a protein capable of binding calcium, for preparing a medicinal product for use in the treatment of individuals contaminated with uranium.

In accordance with said uses, said proteins capable of binding calcium are in particular troponin C or parvalbumin. In such cases, the peptide used corresponds either to the whole protein, or it contains mutations of at least one residue of each helix to a cysteine residue, so as to obtain a cyclic peptide that has an ordered structure of helix-loop-helix type.

The peptides according to the invention are prepared by the conventional techniques of solid-phase or liquid-phase synthesis that are known in themselves to those skilled in the art. The proteins according to the invention are prepared by recombinant DNA techniques, that are known in themselves to those skilled in the art.

Consequently, a subject of the present invention is also an isolated nucleic acid molecule, characterized in that it comprises a sequence encoding a peptide, a polypeptide or a fusion protein, as defined above.

A subject of the invention is also probes and primers, characterized in that they comprise a sequence of approximately 10 to 30 nucleotides that is adjacent to or overlaps a helix-loop-helix type motif, one of the helices or the loop of this motif, of a calcium ion-binding protein as defined above, in particular calmodulin; these probes and these primers make it possible to specifically detect/amplify said nucleic acid molecules encoding a peptide according to the invention.

The nucleic acid molecules according to the invention are obtained by conventional methods, known in themselves, according to standard protocols such as those described in *Current Protocols in Molecular Biology* (Frederick M. AUSUBEL, 2000, Wiley and son Inc., Library of Congress, USA).

The sequences encoding a peptide, a polypeptide or a protein according to the invention can be obtained by amplification of a nucleic acid sequence by PCR or RT-PCR or else by screening genomic DNA libraries by hybridization with a homologous probe. For example, they are amplified by PCR using an appropriate pair of primers as defined above.

A subject of the present invention is also a eukaryotic or prokaryotic recombinant vector, characterized in that it comprises an insert consisting of a nucleic acid molecule encoding a peptide, a polypeptide or a fusion protein as defined above. Many vectors into which a nucleic acid molecule of interest can be inserted in order to introduce it into and to maintain it in a eukaryotic or prokaryotic host cell are known in themselves; the choice of an appropriate vector depends on the use envisioned for this vector (for example, replication of the sequence of interest, expression of this sequence, maintenance of the sequence in extrachromosomal form or else integration into the host's chromosomal material), and also on the nature of the host cell. For example, viral vectors or nonviral vectors such as plasmids can be used.

Preferably, said recombinant vector is an expression vector in which said nucleic acid molecule or a fragment thereof is placed under the control of appropriate transcriptional or translational regulatory elements. In addition, said vector can comprise (tag) sequences fused in-frame with the 5' and/or 3' end of said insert, that are useful for immobilizing and/or detecting and/or purifying the fusion protein, the peptide or the polypeptide expressed from said vector.

These vectors are constructed and introduced into host cells by conventional recombinant DNA and genetic engineering methods which are known in themselves.

A subject of the present invention is also eukaryotic or prokaryotic cells modified with a recombinant vector as defined above.

A subject of the present invention is also a transgenic nonhuman animal organism, characterized in that it comprises cells modified with a nucleic acid molecule as defined above.

A subject of the present invention is also a transgenic plant, characterized in that it comprises cells modified with a nucleic acid molecule as defined above.

A subject of the present invention is also prokaryotic or eukaryotic cells modified with a regulatory system, which reflects the presence of uranium and a light signal. For example, the structure of the peptide according to the invention can be inserted into a regulator or into a repressor of a gene encoding a bioluminescent protein, for example the lux gene; the binding of uranium to this regulator or repressor thus modified allows transcription of the gene and therefore expression of the bioluminescent protein, according to a mechanism similar to that already described for the mercury-sensitive merR repressor (Summers A O et al., Annu. Rev. Microbiol., 1986, 40, 607-634).

The prokaryotic or eukaryotic cells modified with a nucleic acid molecule as defined above and the transgenic plants as defined above, which express proteins enriched in the peptide sequence according to the invention, have an increased capacity for the binding, absorption and accumulation of uranium; they are therefore useful for decontaminating soils and fluids contaminated with uranium.

Consequently, a subject of the present invention is also the use of the prokaryotic or eukaryotic cells modified with a nucleic acid molecule as defined above and of the transgenic plants as defined above, for decontaminating soils and water contaminated with uranium.

The transformed cells as defined above are also useful in particular for producing the peptide, the polypeptide or the fusion protein as defined above.

In addition, the prokaryotic or eukaryotic cells modified with a promoter as defined above are useful for specifically detecting uranium VI.

Consequently, a subject of the present invention is also the use of prokaryotic or eukaryotic cells modified with a promoter as defined above, for preparing a reagent for detecting soils and water contaminated with uranium, and also for diagnosing individuals contaminated with uranium.

A subject of the present invention is also an antibody, characterized in that it binds selectively to the peptide as defined above, in the presence or absence of uranium; such an antibody does not bind to helix-loop-helix type peptides that do not have the mutations as defined above.

The invention encompasses polyclonal antibodies, monoclonal antibodies, chimeric antibodies such as humanized antibodies, and fragments thereof (Fab, Fv, scFv).

Such antibodies are useful for purifying and immobilizing, on an appropriate support, the peptides, the polypeptides and the fusion proteins as defined above, or for detecting uranium in the form complexed with the peptides, with the polypeptides or with the fusion proteins as defined above.

A subject of the present invention is also a kit for detecting a contamination with uranium, characterized in that it comprises at least: a peptide, a polypeptide, a fusion protein or an antibody as defined above, or else a prokaryotic or eukaryotic cell modified with a promoter, as defined above.

BRIEF DESCRIPTION OF THE DRAWINGS

Besides the above arrangements, the invention also comprises other arrangements that will emerge from the description that follows, that refers to examples of use of the antigens and of the antibodies according to the invention, and also to table I that summarizes the sequences of the application, in which the calmodulin residues that have been mutated are indicated in bold and underlined, and to the attached drawings in which:

FIG. 2 illustrates the sequences of the peptides derived from calcium site I which was studied.

DETAILED DESCRIPTION

TABLE I

Figure 1:
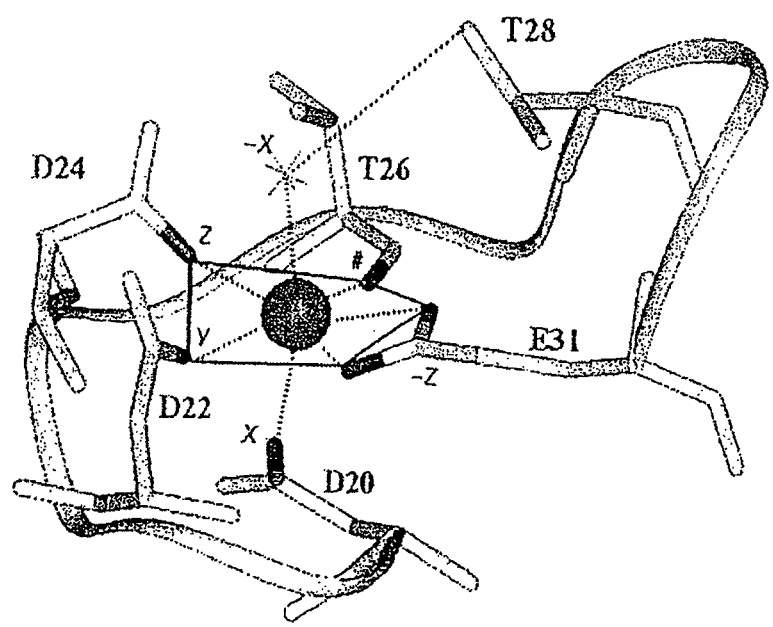
FIG. 1 illustrates, at the top, the three-dimensional structure of *Paramecium tetraurelia* calmodulin site I and the coordination of a calcium ion; at the bottom, calcium-coordinating residues in the four sites.

List of the peptides studied in the application

| Identification No. | Sequence | Name |
|---|---|---|
| SEQ ID No. 1 | EQIAEFKEAFALFDKDGDGTITTKELGTVMRSL | CaM |
| SEQ ID No. 2 | EQIAEFKEAFALCDKDGDGYITTKELGTCMRSL | CaM-M1c |

TABLE I-continued

List of the peptides studied in the application

| Identification No. | Sequence | Name |
|---|---|---|
| SEQ ID No. 3 | EQIAEFKEAFAL<u>C</u>DKDGDG<u>YI</u>TTK<u>D</u>LGT<u>C</u>MRSL | CaM-M2c |
| SEQ ID No. 4 | EQIAEFKEAFAL<u>CT</u>KDGT<u>GYI</u>TTKELGT<u>C</u>MRSL | CaM-M3c |
| SEQ ID No. 5 | EQIAEFKEAFAL<u>C</u>N<u>K</u>NG<u>N</u>G<u>YI</u>TTKELGT<u>C</u>MRSL | CaM-M4c |
| SEQ ID No. 6 | EQIAEFKEAFAL<u>C</u>D<u>KT</u>GT<u>GYI</u>TTKELGT<u>C</u>MRSL | CaM-M5c |
| SEQ ID No. 7 | EQIAEFKEAFAL<u>CTKT</u>GDG<u>YI</u>TTKELGT<u>C</u>MRSL | CaM-M6c |
| SEQ ID No. 8 | RRKWQKTGHAVRAIGRL | MLCKp |
| SEQ ID No. 9 | EQIAEFKEAFAL<u>C</u>S<u>K</u>DG<u>S</u>G<u>YI</u>TTKELGT<u>C</u>MRSL | CaM-M7c |
| SEQ ID No. 10 | EQIAEFKEAFAL<u>CTKT</u>GT<u>GYI</u>TTKELGT<u>C</u>MRSL | CaM-M8c |
| SEQ ID No. 11 | EQIAEFKEAFAL<u>CT</u>KDGDG<u>YI</u>TTKELGT<u>C</u>MRSL | CaM-M9c |
| SEQ ID No. 12 | EQIAEFKEAFAL<u>C</u>DKDG<u>TG</u>YITTKELGT<u>C</u>MRSL | CaM-M10c |

EXAMPLE I

Materials and Methods

1) Peptide Synthesis

The peptides were solid-phase synthesized with an Applied Biosystems automatic peptide synthesizer, model 433A, and by Fmoc chemistry, which uses the fluorenylmethyloxycarbonyl (Fmoc) group for the temporary protection of the α-amine function of amino acids. The protective groups used for the amino acid side chains were tert-butyl ether (tBu) for Ser, Thr and Tyr residues; tert-butyl ester (OtBu) for Asp, Glu; trityl (Trt) for Gln, Asn, Cys; tert-butyloxy-carbonyl (Boc) for Lys; and 2,2,5,7,8-pentamethyl-chroman-6-sulfonyl (Pmc) for Arg.

The coupling reaction was carried out in the presence of an excess of 10 equivalents of amino acid (1 millimole) relative to the resin (0.1 millimole). The latter was first deprotected with respect to the Fmoc group using a 20% piperidine solution. The excess piperidine was removed by washing with N-methyl-pyrrolidone (NMP). The deprotection reaction was monitored by UV-detection at 305 nm of the dibenzo-fulvenepiperidine adducts. In parallel, the amino acid was dissolved in a mixture consisting of 1 ml of NMP and 1 ml of a 1 M solution of 1-N-hydroxy-7-azabenzo-triazole (HOAt) in NMP. A solution of 1 ml of 1 M N,N'-dicyclohexylcarbodiimide (DCC) in NMP was then added so as to form the activated ester of the amino acid. After 40 minutes, this active ester was introduced into the reactor containing the deprotected resin.

At the end of synthesis, the resin was washed several times with dichloromethane (DCM). The cleavage of the peptide and the deprotection of the protective groups of the amino acid side chains were carried out under acidic conditions. The resin was suspended (100 ml per gram of resin) in a solution of 81.5% tri-fluoroacetic acid (TFA), 5% phenol, 5% thioanisole, 5% water, 2.5% ethanedithiol and 1% triisopropylsilane for three hours with stirring at ambient temperature. After filtration over sintered glass, the reaction medium was precipitated with diisopropyl ether and then centrifuged. The pellet was separated from this supernatant and dissolved in TFA. After reprecipitation with ether and centrifugation, the pellet was again dissolved in 20% acetic acid and then lyophilized.

The crude reaction product obtained was purified a first time on a Vydac C18 reverse-phase preparative column (1.0× 25.0 cm) using a 0-60% gradient of acetonitrile in 90 minutes. The pure linear peptide was then lyophilized, and then redissolved in 200 ml of a 100 mM Tris solution, pH 8.0. An equivalent of 5,5'-dithiobis(2-nitrobenzoic) acid was added so as to bring about the specific formation of the intra-molecular disulfide bridge between the two cysteines. The reaction medium was then acidified and then purified using the same protocol as for the crude reaction product. The fractions of pure product were combined and lyophilized. The purity of the product was confirmed by electrospray mass spectrometry.

Stock solutions were prepared by dissolving in water, and the concentrations were determined by spectrophotometry using molar extinction coefficients of 1280 $M^{-1}.cm^{-1}$ for tyrosine, 120 $M^{-1}.cm^{-1}$ for the disulfide bridge and 5690 $M^{-1}.cm^{-1}$ for tryptophan.

2) Metals

All the metal salts used are nitrates (>99.9% purity, Aldrich, France). The stock solutions are acidified to pH=2 with nitric acid so as to prevent the formation of hydroxides.

3) Fluorescence

The fluorescence spectra are recorded on a Cary Eclipse spectrometer (Varian, France) equipped with a thermostated cuvette holder. The excitation wavelength used is 280 nm with slot widths of 10 nm for excitation and of 2.5 nm for emission. The spectra are recorded between 300 nm and 450 nm in a cuvette with a 1 cm optical path.

4) Time-resolved Laser Spectrofluorimetry (TRLS)

A Nd-YAG laser (minilite model, Continuum) operating at 266 nm and delivering an energy of 1 mJ in 4 ns pulses at a frequency of 20 Hz was used as excitation source. The beam was directed into a 4 ml quartz cuvette, and then into the measuring cell of the "Fluo 2001" spectrofluorimeter (Dilor, France) by means of quartz lenses. The light was then concentrated at the inlet of a polychromator, and the signal was detected using an array of 1024 photodiodes cooled using the Peltier effect (−30° C.). The spectra were recorded by integrating the signal detected by the photodiodes for a period of 0.5 s. An electronic circuit synchronized with the Laser made it possible to carry out the detection after a delay of 90 μs for a period of 50 μs. The assembly was controlled by a computer (Dell).

5) Electrospray Mass Spectrometry (ESI-MS)

The positive-detection-mode electrospray mass spectra were recorded with a Q-TOF II device (Micromass). The sample to be analyzed was introduced into the source via a syringe pump (Harvard Apparatus). Nitrogen was used as drying and collision gas with a source heated to 80° C. The cone voltage was 30 volts, and a high voltage of 3500 kV was applied to the capillary. The sample solution flow rate was fixed at 5 µL.min$^{-1}$. The spectra represent the mean of 40 scans recorded between 400 and 3000 m/z at a scan rate of 6 s/scan.

6) Circular Dichroism (CD)

The CD spectra were recorded with a CD6 device (Jobin Yvon) equipped with a thermostated cuvette holder and computer-controlled using the CDMax program. The compounds were solubilized at a concentration of 5 µM in a 1 mM MES buffer at pH 6.5.The spectra were recorded at ambient temperature between 180 nm and 250 nm using a cuvette with a 0.1 mm optical path. Each spectrum represents the mean of 4 successive accumulations obtained with an integration time of 0.5 s and a step of 0.5 nm. The spectra were smoothed using the algorithm included in the CDMax program.

EXAMPLE 2

Preparation of Cyclic Peptides Derived from Calmodulin Site I and Analysis of the Heavy Metal Chelation 1) Preparation of Cyclic Peptides The linear peptide of 33 residues corresponding to calmodulin site I (CaM: EQIAEFKEAFALFDKDGDGTITT-KELGTVMRSL, SEQ ID No. 1) tested by circular dichroism exhibits no ordered structure, even when placed in the presence of an excess of calcium ions. At high concentration (100 µM), it aggregates in solution, probably because of the intermolecular interactions between the hydrophobic portions of the non-structured helices.

Consequently, in order to prevent these interactions that are unfavorable to the formation of a stable native helix-loop-helix structure, peptides comprising a disulfide bridge connecting positions 13 and 29 of said peptide, corresponding, respectively, to positions 19 and 35 in the calmodulin sequence, were prepared. Consequently, peptides comprising the mutations Phe19Cys and Val35Cys were synthesized. In addition, the mutation Thr26Tyr was inserted in order to make it possible to introduce a fluorescent probe into the coordinating loop, in such a way as to monitor the binding of the metal. In addition, the glutamic acid at position 25 of the peptide or at position 31 of calmodulin was optionally mutated to aspartic acid (Glu31Asp).

The peptides synthesized have the following sequences (FIG. 2 and table I), in which the mutations are indicated in bold:

```
CaM-M1c:
                                        (SEQ ID No. 2)
EQIAEFKEAFALCDKDGDGYITTKELGTCMRSL

CaM-M2c:
                                        (SEQ ID No. 3)
EQIAEFKEAFALCDKDGDGYITTKDLGTCMRSL
```

2) Analysis of the Structure and of the Affinity of the Cyclic Peptides for Heavy Metals (Peptides CaM-M1c and CaM-M2c)

a) Peptide Cam-M1c

The corresponding peptide CaM-M1c was synthesized and its affinity with respect to various metals was tested by mass spectrometry, circular dichroism (CD) and time-resolved fluorescence (TRLS). The CD spectra recorded in the presence of 8 equivalents of metals show good affinity for calcium, cadmium, terbium, europium and uranium, and also a weak affinity with cobalt. No interaction is detected with the other elements of the alkaline earth metal column (Mg, Sr, Ba).

Figure 3:
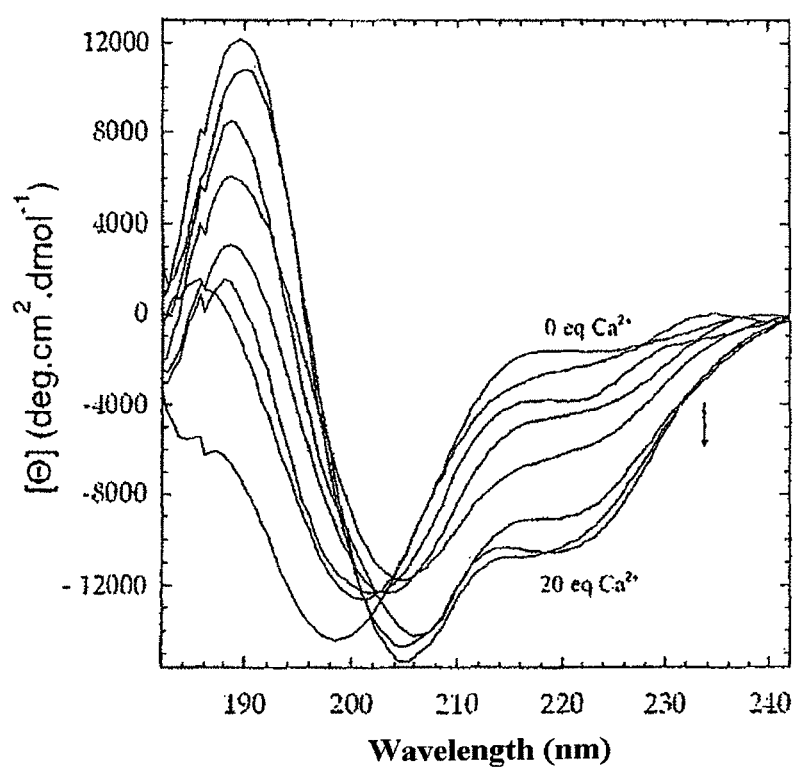
FIG. 3 illustrates the circular dichroism spectra of a 50 µM solution of the cyclic peptide CaM1c in the presence of calcium ions in 10 mM MES (pH 6.5), added at concentrations equal to 0, 0.2, 0.5, 1.0, 2.0, 5.0 and 20 equivalents.
Figure 4:
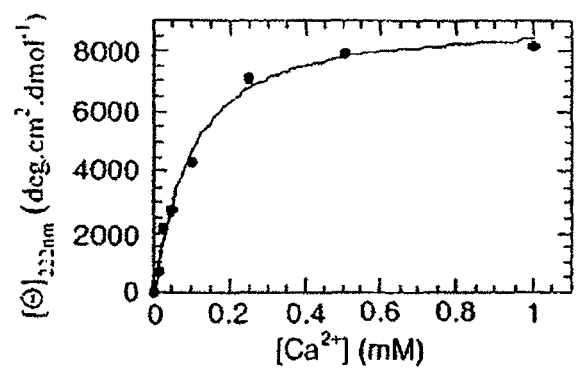
FIG. 4 illustrates the variations in circular dichroism intensity at 222 nm of the peptide CaM-M1c, as a function of the molar concentration of calcium, and its fit to the binding isotherm curve.

The circular dichroism (CD) analysis of the peptide CaM1c shows a spectrum typical of a disordered structure with a minimum at 190 nm (FIG. 3). The absence of a secondary structure was confirmed by proton nuclear magnetic resonance (1H NMR) spectroscopy. When dissolved calcium is added, the CD spectrum takes on a form that is typical of a helicoidal conformation with minima at 206 and 222 nm. A CaM1c titration by CD was then carried out and the intensity of the dichroic signal at 222 nm was reported as a function of the concentration of calcium ions added (FIG. 4). The binding isotherm curve which goes through the experimental points demonstrates a Ca/peptide stoichiometry of 1/1 and makes it possible to calculate a dissociation constant Kd of 30 µM.

The mass spectrum of the peptide in the absence of the metal shows three main peaks at 736.8, 920.7 and 1227.3 m/z, corresponding to the five-, four- and three-times protonated peptide, respectively. The introduction of the increasing concentrations of calcium to the peptide leads to a modification of this spectrum, with new peaks at 744.7, 930.6 and 1240.5 m/z, compatible with a 1:1 peptide:calcium complex exhibiting the same charge state. Assuming that the peptide free of metal and the complex have similar signal responses, a dissociation constant can be calculated, as described by Whittal et al. (Prot. Sci., 2000, 9, 332-343), giving a Kd=30 µM (table II), in agreement with the value calculated by the CD titration.

Figure 5:
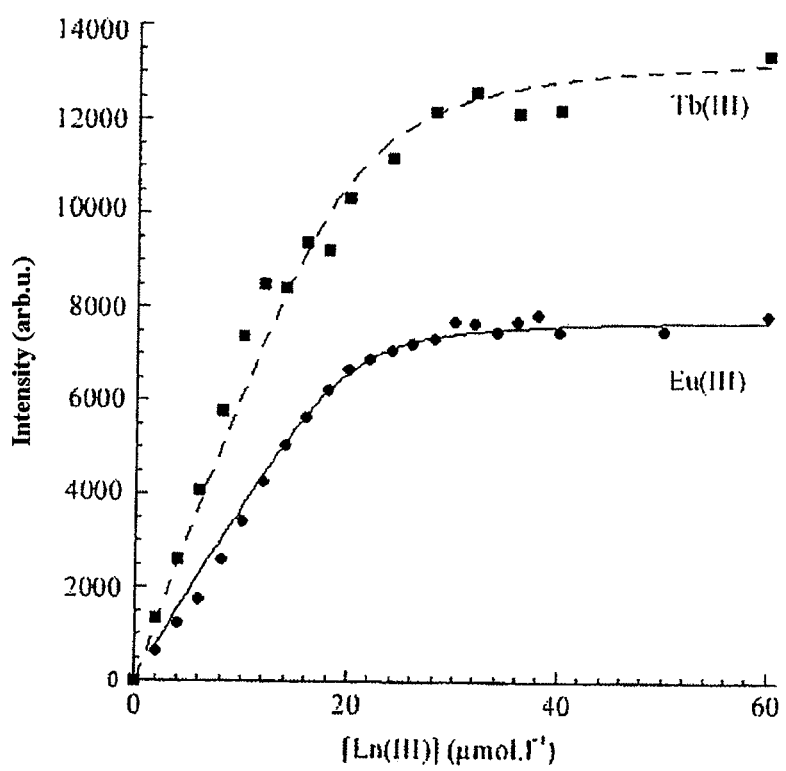
FIG. 5 illustrates the variations in fluorescence intensity at maximum emission as a function of the molar concentration of terbium ions (at 545 nm) and europium ions (at 618 nm), added to the peptide CaM-M1c. The curves represent the binding isotherms fitted to the experimental points.

The lanthanide ions have often been used as calcium models in biological studies of molecules (Linse et al., J. Biol. Chem., 1991, 266, 8050-8054). Spectrofluorimetry titrations of the peptide CaM-M1c (20 µM solution in 10 mM MES buffer, pH 6.5) with solutions of terbium and of europium were carried out by time-resolved laser fluorescence (TRLS) (FIG. 5). This spectroscopy is based on excitation of the metal, followed by time resolution of the fluorescent signal, thus overcoming the limitations due to the presence of fluorophores whose fluorescence has a short life span but is of strong intensity (Whittal et al., mentioned above). Using an excitation wavelength of 266 nm, the fluorescence emission of the two lanthanides is observed by means of an energy transfer mechanism via Tyr20 of the peptide, with an increase in the fluorescence emitted from the metal up to a limit corresponding to a lanthanide:peptide ratio of 1:1. For terbium, the stronger emission is located at 545 nm. In the case of europium, the spectrum shows fluorescence emission maxima at 593 and 618 nm. The measurements of fluorescence emission intensity (545 nm for Tb3+ and 618 nm for Eu3+) as a function of lanthanide concentration and the fit of these data with respect to the binding isotherm lead to the determination of the dissociation constants Kd(Tb3+)=3.5 µM and Kd(Eu3+)=0.6 µM (table II).

Figure 6:
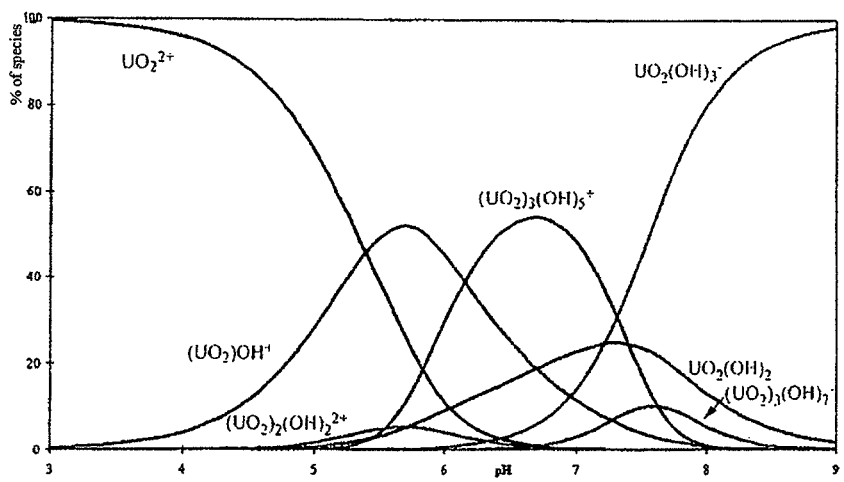
FIG. 6 represents the speciation diagram for uranium (VI) at a concentration of 1 µM.

In the case of uranyl ions, the study of the binding of uranyl ions to the peptide is made difficult by the complex speciation of this metal in water (FIG. 6). Specifically, at pH 6.5, the speciation diagram shows that the predominant species are $(UO_2)_3(OH)_5^+$ (67%) and $(UO_2)(OH)^+$ (17%). At this pH, only 5% of uranyl ion $UO_2^{2+}$ remains. Analysis of the complex formed with the peptide by mass spectrometry shows that the uranium is coordinated in the $UO_2^{2+}$ form. Now, all uranium species are fluorescent, and it becomes difficult, with conventional fluorescence methods, to monitor just one of the species present in solution. This problem was resolved with TRLS, which is based on the following principle: after an excitation by laser pulse, the fluorescence is detected after a delay chosen by the user; a delay of 80 µs made it possible to do away with all the species other than $UO_2OH^+$ for the detection. Under these instrumental conditions, using an excitation wavelength of 266 nm, a 2 µM solution of $UO_2(NO_3)_2$ was titrated by means of successive additions of aliquots of an aqueous solution of the peptide. This experiment made it possible to determine a dissociation constant $K_d$ of 4.7 µM, table II.

TABLE II

Dissociation constants for the complexes formed with CaM-M1c in an aqueous medium at pH 6.5

| | Metal | | | | |
|---|---|---|---|---|---|
| | Ca (II) | Cd (II) | U* (VI) | Tb (III) | Eu (III) |
| Kd (µM) | 30 ± 1[a,c] | 8 ± 4[a] | 4.7 ± 0.6[b] | 1.5 ± 0.6[b] | 0.6 ± 0.2[b] |

[a]Titration by CD,
[b]titration by TRLS,
[c]titration by ESI/MS
*The species titrated is the $UO_2(OH)^+$ entity.

b) Peptide CaM-M2c

A second peptide comprising an additional mutation, namely: substitution of the glutamic acid at position 31 of the calmodulin sequence to aspartic acid (Glu31Asp), was also synthesized. The side chain of the amino acid is shortened by a methylene group, and the cavity formed by the loop is therefore greater in size. The same ESI/MS, CD and TRLS studies show that this peptide loses the affinity for all divalent metals, and for the uranyl ion. Only the affinities for the lanthanides are conserved, with dissociation constants of 3.5±1 µM and 3.2±0.8 µM for terbium and europium, respectively.

All the results show that the cyclic peptides studied, containing the mutations Phe19Cys, Val35Cys and Thr26Tyr and, optionally, the mutation Glu31Asp, and in which cysteines 19 and 35 are connected by a disulfide bridge, have the following properties:
  unlike the linear peptide corresponding to calmodulin site I (peptide CaM), which does not exhibit an ordered structure and aggregates in solution, the cyclic peptides synthesized have a stable helix-loop-helix type structure, and
  they are capable of binding metal ions, including uranium VI (peptide CaM-M1c), with an affinity comparable to that of native calmodulin for the calcium ion.

These results also indicate that point mutations in the sequence of the loop of calmodulin site I make it possible to vary the relative affinity of the peptides for various metal ions. However, none of the mutant peptides studied specifically binds uranium VI.

EXAMPLE 3

Preparation of Cyclic Peptides Specific for Uranium VI

1) Peptide Synthesis

The peptides synthesized correspond to cyclic peptides containing the mutations Phe19Cys, Val35Cys and Thr26Tyr, as described in example 2, and also the following additional mutations:
  D20T (peptide CaM-M9c)
  D24T (peptide CaM-M10c)
  D20T and D24T (peptide CaM-M3c)
  D20S and D24S (peptide CaM-M7c)
  D20T and D22T (peptide CaM-M6c)
  D22T and D24T (peptide CaM-M5c)
  D20N, D22N and D24N (peptide CaM-M4c)
  D20T, D22T and D24T (peptide CaM-M8c)

More specifically, the sequences of these peptides, in which the mutated residues are indicated in bold, are represented in FIG. 2 and in table I.

Figure 7:
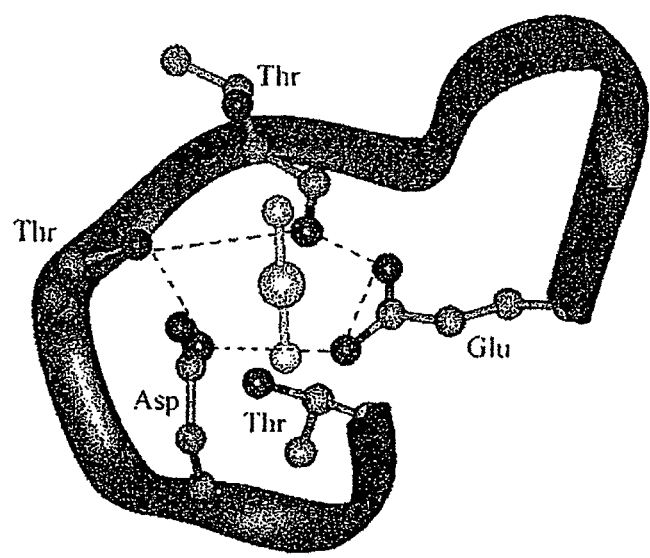
FIG. 7 is a diagrammatic representation of uranyl in the coordinating loop of calmodulin that has been mutated (peptide CaM-M3c), obtained from the three-dimensional structure of the calmodulin loop (PDB code: 1EXR)

A diagrammatic representation of uranyl in the coordinating loop of calmodulin that has been mutated (peptide CaM-M3c), obtained from the three-dimensional structure of the calmodulin loop (PDB code: 1EXR), is given in FIG. 7.

2) Analysis of the Affinity of the Peptides for Various Metal Ions (Peptides CaM-M3c, CaM-M4c and CaM-M5c)

The affinity of the peptide CaM-M3c for various metal ions ($Ca^{2+}$, $Mg^{2+}$, $Ba^{2+}$, $Sr^{2+}$, $Tb^{3+}$, $Eu^{3+}$, $UO_2^{2+}$) was tested using two spectroscopic methods: circular dichroism (CD) and electrospray mass spectrometry (ESI-MS).

The CD spectra and the positive-detection-mode electrospray mass spectra (ESI-MS) were recorded as described in example 1.

Figure 8:
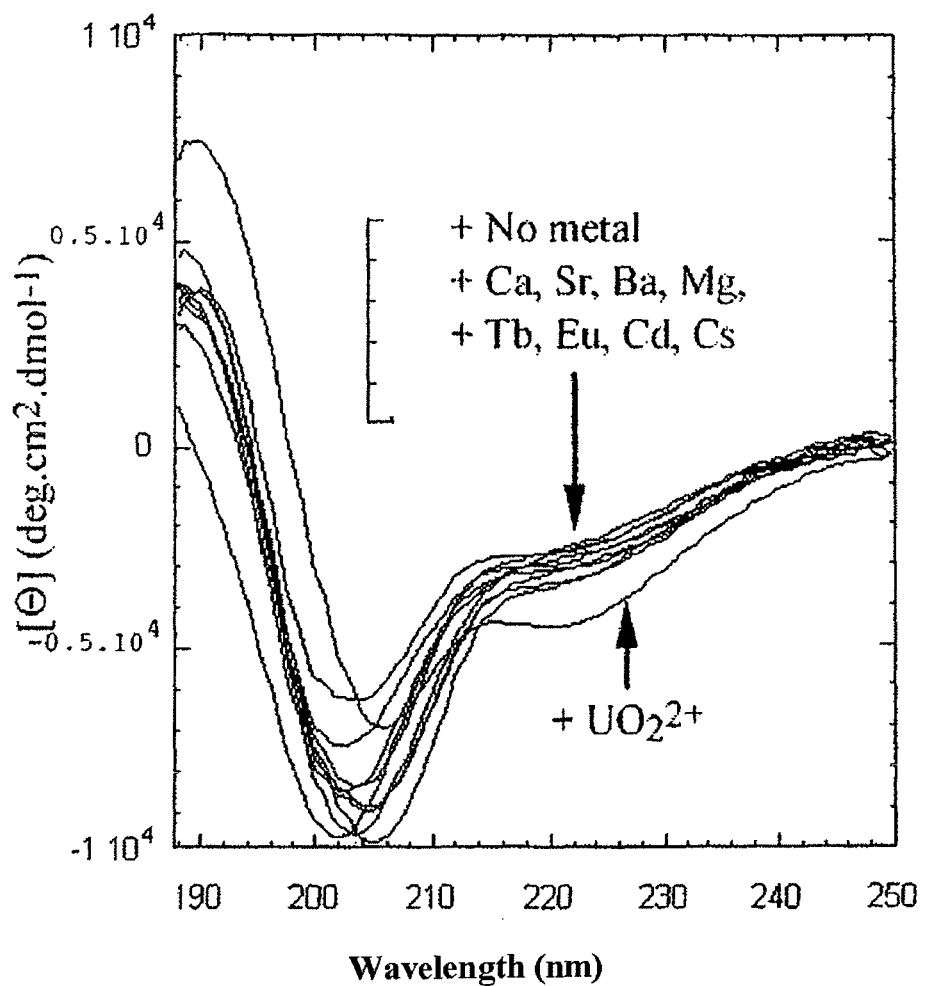
FIG. 8 illustrates the dichroic spectra of a 20 µM solution of the peptide CaM-M3c in 1 mM MES buffer, in the presence of 8 equivalents of various metals.

FIG. 8 shows that only the addition of an excess of uranyl results in a modification of the dichroic spectrum of the peptide CaM-M3c. In this case, two new minima at 207 nm and 222 nm are observed. They are characteristic of an α-helical ordered secondary structure. This result is confirmed by the ESI-MS analysis: only the addition of uranyl in solution results in the appearance of a mass peak compatible with the formation of a 1/1 peptide/$UO_2$ complex.

The peptides CaM-M4c, CaM-M5c, CaM-M6c, CaM-M7c, CaM-M8c, CaM-M9c and CaM-M10c gave the same results in circular dichroism spectroscopy and mass spectroscopy (ESI-MS), which indicates that these peptides do not bind calcium, the lanthanides and the other ions tested, but only uranium (VI).

3) Analysis of Uranium Coordination by the Peptide CaM-M3c a) Problem to be Solved (Speciation)

The analysis of the coordination of the uranyl ion by a biological molecule is envisaged at a pH close to the physiological value, i.e. between 6 and 8. Now, at this pH, the uranyl ion is no longer in solution only in a single form, $UO_2^{2+}$, but in the form of various complexes derived from this metal core: hydroxo and carbonate complexes, for example. This phenomenon is referred to as speciation. The amount of each of the species present in an aqueous solution depends on the concentration of uranium, on the concentration of dissolved gases (carbonates) and on the thermodynamic parameters associated with the metal ion. At a concentration of 1 µM with respect to uranium, the speciation diagram (FIG. 6) shows that the predominant species at pH 6.5 are the species $(UO_2)_3(OH)_5^+$, $UO_2(OH)_2$ and $UO_2(OH)^+$, representing, respectively, 52.1, 16 and 25.3% of the U(VI) in solution. The minor species are $UO_2^{2+}$, $UO_2(OH)_3^-$ and uranium/carbonate complexes.

In a titration experiment by conventional fluorescence, each of these uranium species contributes to the overall intensity of fluorescence detected after excitation. The calculation of a dissociation constant is consequently impossible, since it is not possible to isolate the contribution of each of the species present in solution. For this reason, the titrations were carried out using time resolution, i.e. the difference in the lifetime of fluorescence of each of the species involved, as described in example 1. Using a delay of greater than or equal to 70 µs between the laser shot (excitation) and the detection, the only species detected is the monohydroxo complex $UO_2(OH)^+$.

b) Analysis of Uranium Coordination by the Peptide CaM-M3c in Various Media $b_1$) Analysis Of Uranium Coordination in Water 2 µM uranium was titrated with the peptide CaM-M3c in a pure aqueous medium, the pH of which is adjusted to 6.5 with aqueous ammonia. The time resolution parameters (70 µs delay, 100 µs gate width, 0.5 s integration) make it possible to visualize only the monohydroxylated uranium species.

Figure 9:
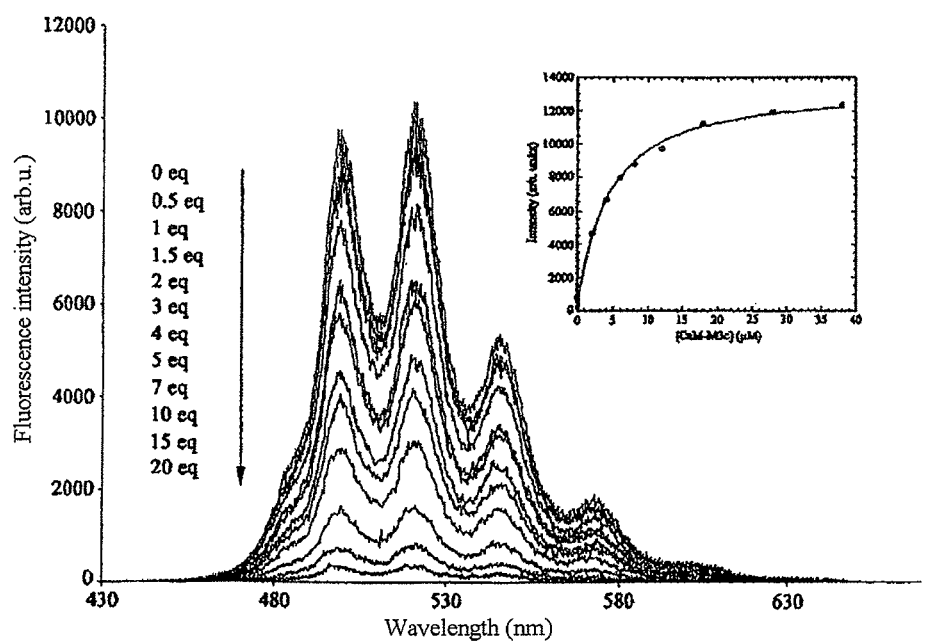
FIG. 9 illustrates the fluorescence spectra corresponding to the titration, with the peptide CaM-M3c, of a 2.0 µM solution of uranyl nitrate in water at pH 6.5.

When increasing amounts of peptide are added to the initial solution of uranium, the intensity of the fluorescence of $UO_2(OH)+$ decreases, attesting to the coordination of the metal with the peptide. The graph of the intensity at 520 nm as a function of the concentration of peptide added can be simulated by the theoretical expression corresponding to the chemical equilibrium involved, taking into account the fact that the concentration of $UO_2(OH)+$ in solution is equal to 17.21% of the U(VI) introduced. The dissociation constant corresponding to the equilibrium $UO_2(OH)+CaM-M3c \rightarrow (CaM-M3c)(UO_2)+OH^-$ is calculated from the simulation: Kd=3.8±0.3 µM (FIG. 9).

$b_2$) Analysis of Uranium Coordination in a Phosphate Medium

In a second experiment, the uranium chelation by the peptide was studied in a 1 mM phosphate buffer medium, at pH 6.5. In this medium, the uranyl initially forms complexes with the phosphate ions, the thermodynamic data of which are as follows:

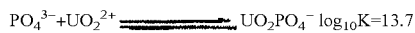
$PO_4^{3-}+UO_2^{2+} \rightleftharpoons UO_2PO_4^-$  $\log_{10}K=13.7$

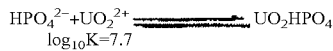
$HPO_4^{2-}+UO_2^{2+} \rightleftharpoons UO_2HPO_4$
$\log_{10}K=7.7$

$H_3PO_4+UO_2^{2+} \rightleftharpoons UO_2H_2PO^++H^+$
$\log_{10}K=1.1$ The uranium/phosphate complexes have the particularity of increasing the intensity of fluorescence of the metal ion, whereas the other known ligands bring about an attenuation of the fluorescence.

Figure 10:
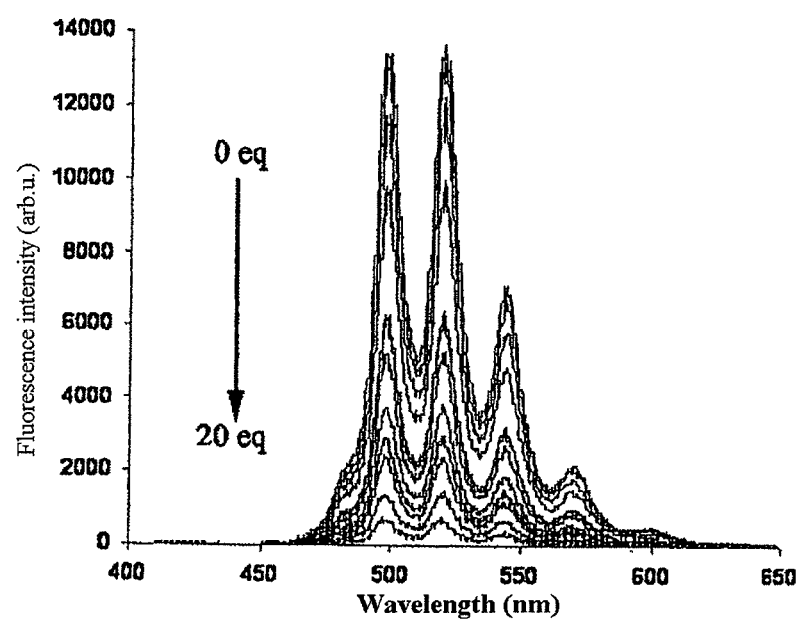
FIG. 10 illustrates the fluorescence spectra corresponding to the titration, with the peptide CaM-M3c, of a 2.0 µM solution of uranyl nitrate in 1 mM phosphate buffer, pH 6.5.

Fractions of an aqueous solution of the peptide were added successively to a 2.0 µM solution of $UO_2(NO_3)_2$ in a 1 mM phosphate buffer at pH 6.5. The fluorescence spectrum of the uranyl ion ($\lambda_{ex}$=266 nm) was recorded after each addition. All the spectra obtained are represented in FIG. 10.

Figure 11:
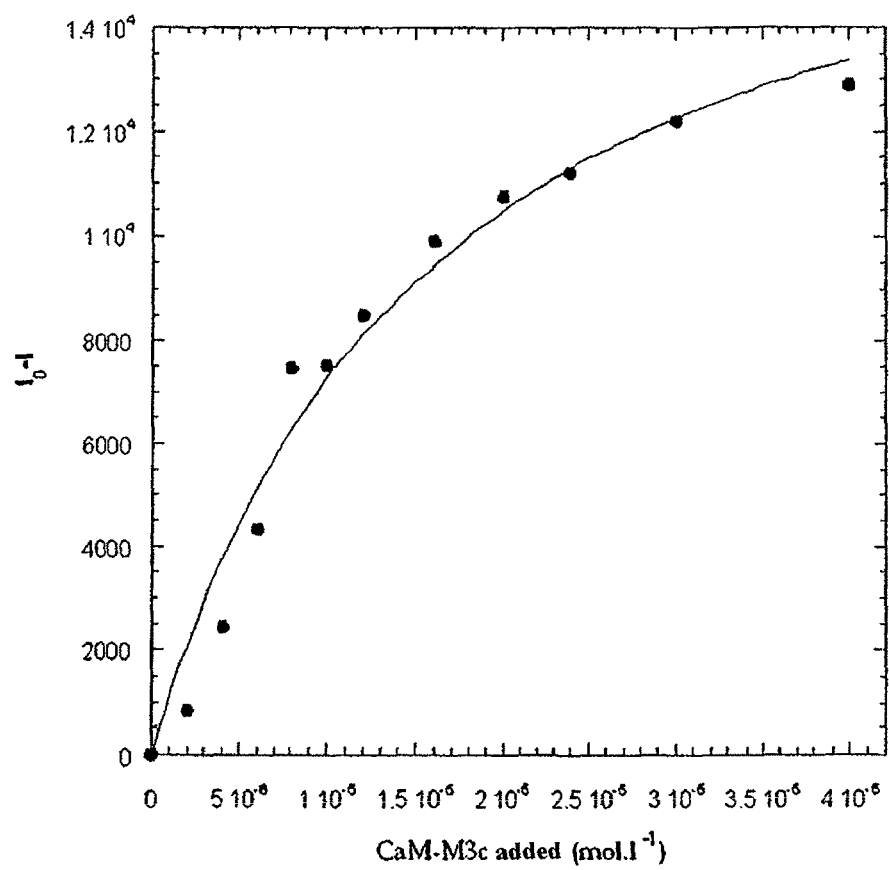
FIG. 11 illustrates the variation in the intensity of fluorescence emission (at 520 nm) of a 2.0 µM solution of uranyl nitrate in 1.0 mM phosphate buffer, as a function of the amount of peptide CaM-M3c, and its fit with the relative binding isotherm equation.

The graph of the intensity at 520 nm as a function of the concentration of uranium added is then simulated by the binding isotherm corresponding to the formation of a 1/1 complex between uranium and the peptide, according to the relationship deduced from the expression of the dissociation constant:

$$I_0 - I = \frac{(I_0 - I)_{max}}{4[U]_0}\left[4[U]_0 + \frac{K_d}{[P]} - \sqrt{\left(4[U]_0 + \frac{K_d}{[P]}\right)^2 - 16[U]_0^2}\right] \quad (1)$$

where $[U]_0$=2.0 µM, $K_d$ is the dissociation constant of the complex, and [P] denotes the amount of peptide added in solution. The experimental data and also the interpretation thereof by means of equation (1) are represented in FIG. 11. The dissociation constant calculated by this approach is 18 µM.

$b_3$) Analysis of the Uranium Coordination in the Presence of Other Ions

The uranium coordination by the peptide was also studied in the presence of a mixture of other ions. The composition of the reaction medium corresponds to an average of the ion composition of several French spring waters, from which the carbonate ions, which are inhibitors of uranyl fluorescence, have been removed. The exact composition of the medium tested is as follows:

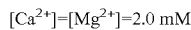
$[Ca^{2+}]=[Mg^{2+}]=2.0$ mM

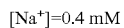
$[Na^+]=0.4$ mM

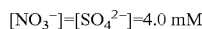
$[NO_3^-]=[SO_4^{2-}]=4.0$ mM

pH=6.5.

Figure 12:
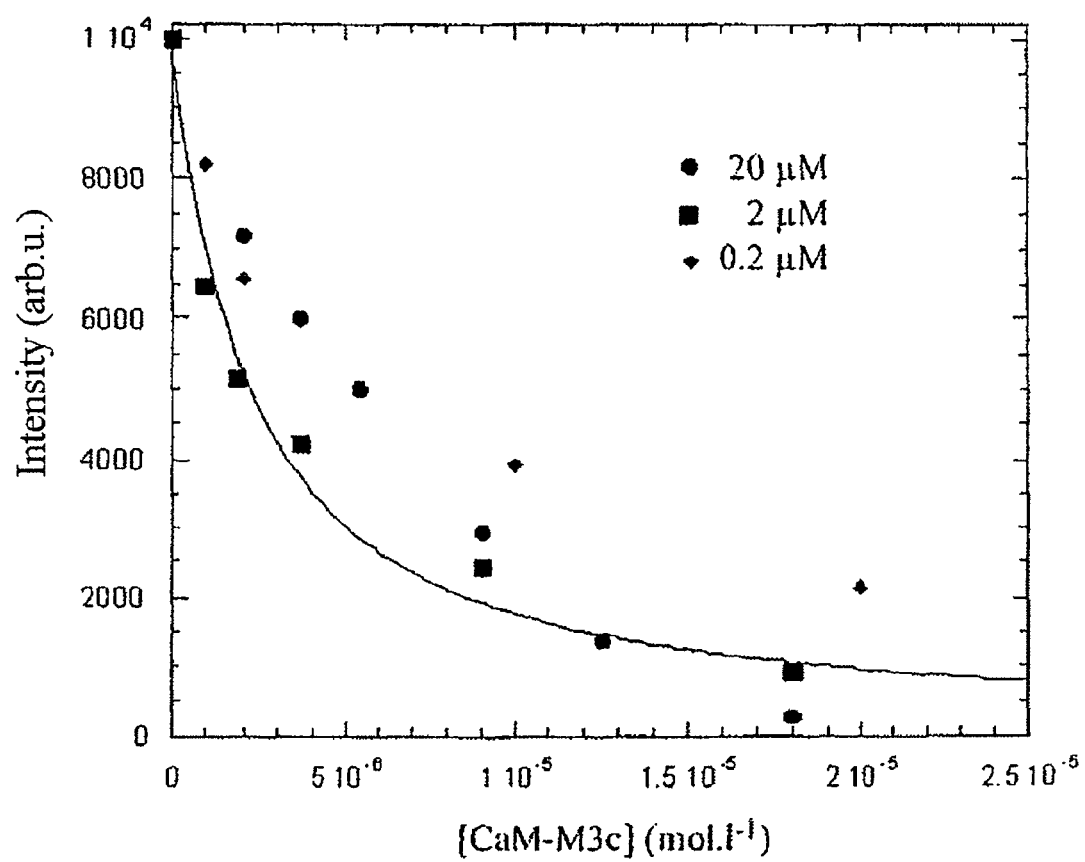
FIG. 12 illustrates the decrease in fluorescence of 20.0, 2.0 and 0.2 µM uranyl nitrate solutions in the presence of 2.0 mM calcium, 2.0 mM magnesium and 0.4 mM sodium metal ions (and of 1.0 mM phosphate buffer), as a function of the amount of peptide CaM-M3c. This experiment mimics a titration of the uranium present as a contaminant in spring water.

This medium is artificially contaminated with increasingly low concentrations of uranium (20 µM, 2 µM, 0.2 µM). In each case, the peptide is added until complete extinction of the uranium fluorescence is obtained (FIG. 12).

The apparent dissociation constants calculated for each of these titrations are 10±1 µM. They are of the same order of magnitude as the dissociation constant calculated in deionized water at pH 6.5 and in phosphate buffer. This demonstrates the absence of competition, firstly, between U(VI) and the other metal cations and, secondly, between the peptide and the other uranium ligands: the peptide CaM-M3c is therefore selective for uranium under these conditions.

The results obtained show that the peptide CaM-M3c, which has the mutations D20T and D24T, is selective for uranium VI. In the concentration range studied (0.1 µM to 2.0 mM with respect to metals), the peptide CaM-M3c coordinates uranium with a dissociation constant of between 3.8 and 18 µM in the various media tested. No measurable affinity for Mg, Ca, Sr, Ba, Eu or Tb is detected.

EXAMPLE 4

Analysis of the Interaction of Uranium with Native Bovine Brain Calmodulin

1) Analysis of Uranium Coordination by the Bovine Brain Calmodulin Protein

Figure 13:
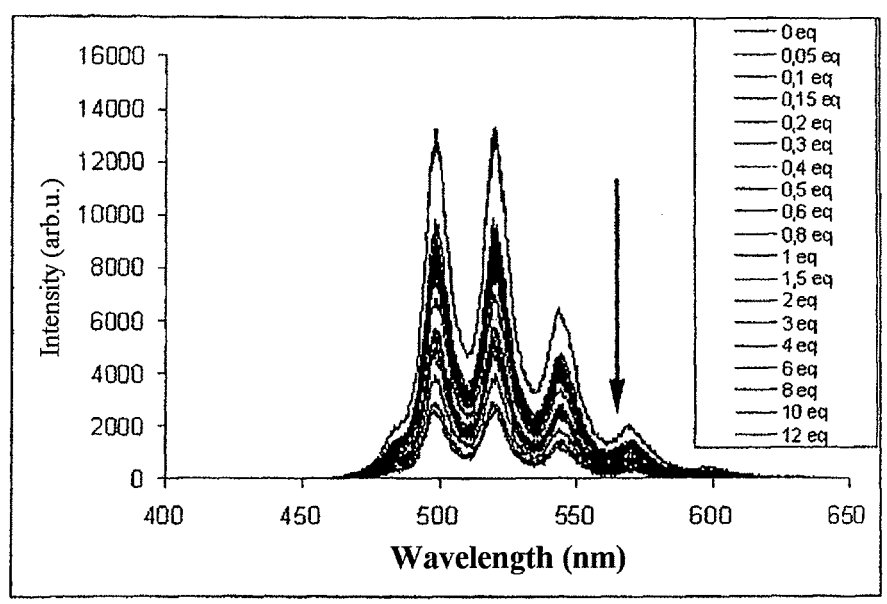
FIG. 13 illustrates the spectra of titration, with the calmodulin protein, of a 2.0 µM solution of uranyl nitrate in 1.0 mM phosphate butter (pH 6.5)
Figure 14:
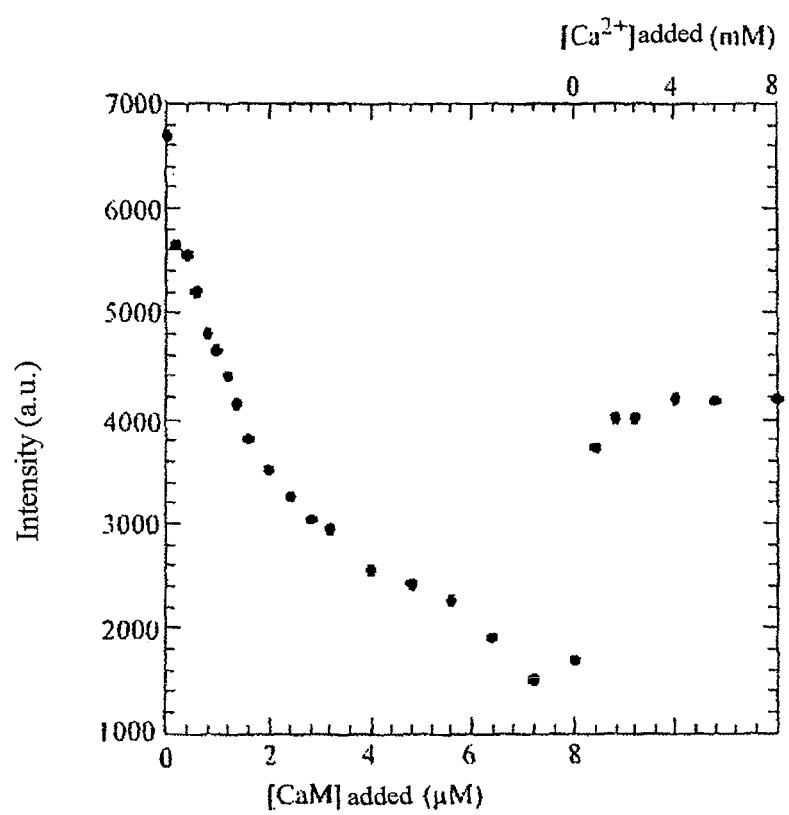
FIG. 14 illustrates the titration, by TRLS, of a 0.4 µM solution of uranyl nitrate in 1.0 mM phosphate buffer (pH 7.0), with a solution of calmodulin (0 to 8 µM), and then titration of the final mixture with calcium (from 0 to 8 mM). Each point represents the value of the intensity recorded at the maximum of the spectrum of the free uranyl ion in solution, corrected with respect to the variations in intensity of the Laser shot.
Figure 16:
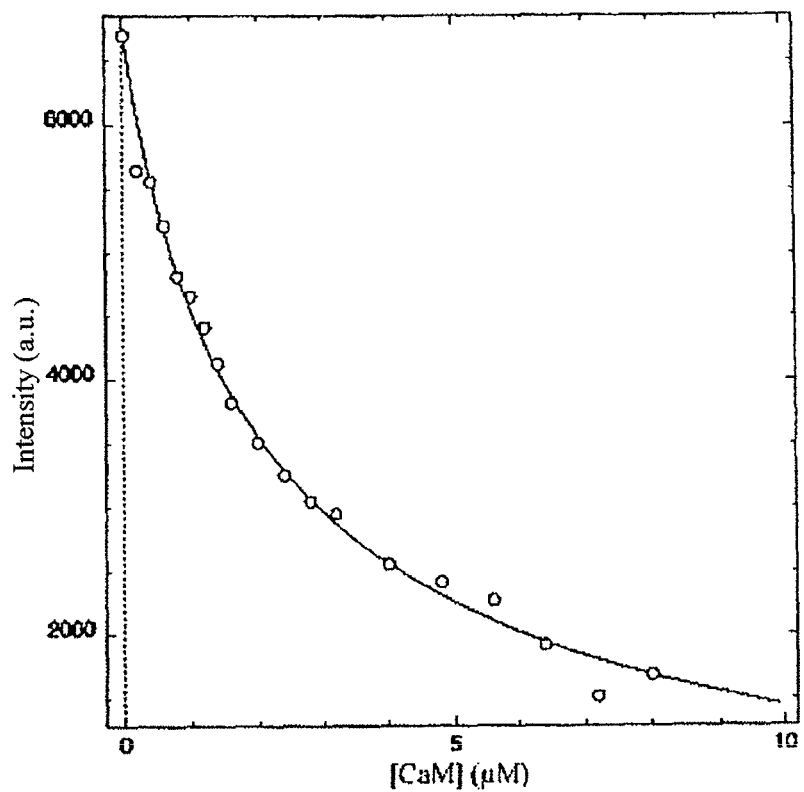
FIG. 16 illustrates the simulation of the experimental points obtained in the experiment of titration of a 0.4 µM uranyl solution with calmodulin, using the Dynafit program. Four simulations were proposed to the program, taking into account from 1 to 4 high-affinity sites for uranium per protein molecule. Only the curve corresponding to 2 sites is represented here, since it alone results in a correct simulation of the experiment, and FIG. 17 corresponds to the simulation of the experimental points obtained in the experiment of competition between calcium and uranyl for calmodulin, obtained with the Dynafit program, considering that each calmodulin protein monomer contains two sites that are independent of one another.
Figure 17:
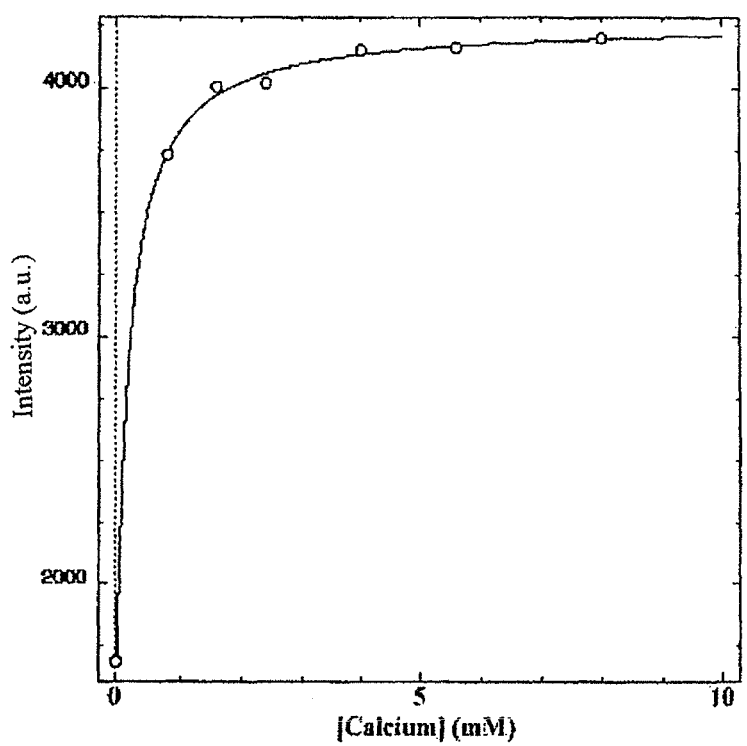

The coordination of uranium (in uranyl form, 2.0 µM) by the native protein in 1 mM phosphate medium was also studied. The complexation of uranium with the protein is reflected by a drop in uranyl fluorescence intensity. The titration spectra are represented in FIG. 13. In another experiment, a 0.4 µM solution of uranyl nitrate in a 1.0 mM phosphate buffer (pH 7.0) was titrated with a solution of calmodulin up to a protein concentration of 8 µM. After the addition of 8 µM of calmodulin, calcium ions were added up to the concentration of 8 mM (FIG. 14). The values for the titration of uranyl by calmodulin were interpreted by simulating the experimental data with a system of equations corresponding to one, two, three or four independent sites for uranium (FIG. 16). The Dynafit software (Kuzmic, P. 1996, *Anal. Biochem.* 237, 260-273) was used for these simulations. Only the system taking into account two high-affinity sites gave an acceptable simulation, with dissociation constants of 3.3±0.4 µM and 0.72±0.2 µM for each of the two sites. The values for competition with the calcium ions were also interpreted with a system of suitable equations and the simulation of the experimental points with this system is given in FIG. 17. The simulation was carried out by considering that, in the presence of 8 µM of calmodulin and 0.4 µM of uranyl, each of the two high-affinity sites is occupied by uranium in an equi-probable manner. It is also considered, as a hypothesis, that each of these two sites is independent of the other. The simulation is therefore carried out with a system of four chemical equilibria: two corresponding to the dissociation equilibria of the "site-uranium" complexes, and two corresponding to the displacement of uranium by calcium in each of the sites. The simulation confirms that just one of the two sites complexed with uranium is displaced by calcium. This shows that the calmodulin protein can bind uranium in calcium complexation sites.

2) Interaction of the Protein with its Ligand in the Presence of Uranium

In the presence of calcium, calmodulin can bind and activate a large diversity of targets. Among these, the MLCKp peptide, which has 17 residues and is derived from the calmodulin-binding domain of a rabbit muscle myosin light chain kinase (CALBIOCHEM), has the following sequence:

Ac-RRKWQKTGHAVRAIGRL-NH$_2$ (SEQ ID No. 8).

Two series of experiments were carried out in order to verify that the protein can still interact with this ligand in the presence of a uranyl ion.

In a first series, a fluorescence spectrum for the tryptophan of the ligand, dissolved at a concentration of 5 µM in a 10 mM MES buffer, at pH 6.5, was recorded as described in example 1.

Excitation of the solution at 280 nm makes it possible to detect an emission at 350 nm, characteristic of a tryptophan fluorescence transition. On the other hand, with uranium, the tryptophan de-excites via the metal, which exhibits energy levels corresponding to a fluorescent transition. The emission detected is then that of the metal ($\lambda$>450 nm) and no longer that of the tryptophan. This energy transfer phenomenon shows, in addition, that the uranium is, in this complex, located less than 15 Å (maximum distance for energy transfer) from the tryptophan, which is in agreement with the distances measured on the X-ray structure (10 Å and 6.5 Å) between the tryptophan of the peptide and two of the four calciums.

These results indicate that calmodulin-derived chameleon proteins comprising the sequence of at least one peptide according to the invention can, in the presence of uranium, bind the MLCK substrate peptide and can therefore be used as uranium VI-specific biosensors.

EXAMPLE 5

Comparative Analysis of the Affinity and of the Specificity of the Peptides for Uranium and Terbium The compared affinities for $UO_2^{2+}$ and $Tb^{3+}$ of the calmodulin site I-derived peptides, mutated at the residues as indicated in table III below, were measured in 1 mM phosphate medium, pH=7, by the technique as described in example 1.

The results are given in table III below.

TABLE III

| | Compared affinities of the peptides for $UO_2^{2+}$ and $Tb^{3+}$ | | | | | | |
|---|---|---|---|---|---|---|---|
| Peptide | Charge | Res20 | Res22 | Res24 | Res31 | Kd (µM) $UO_2^{2+}$ | Kd $Tb^3$ | Kd $Ca^{2+}$ |
| CaM-M1c | 4 | D | D | D | E | 6.8 | 4 µM | 30 µM |
| CaM-M2c | 4 | D | D | D | D | >1000 | 36 µM | >10 Mm |
| CaM-M3c | 2 | T | D | T | E | 18 | 15 mM | >10 mM |
| CaM-M4c | 1 | N | N | N | E | 26 | 12 mM | >10 mM |
| CaM-M5c | 2 | D | T | T | E | 9.8 | 23 mM | >10 mM |
| CaM-M6c | 2 | T | T | D | E | 29 | 8.3 mM | >10 mM |
| CaM-M7c | 2 | S | D | S | E | 53 | 9.3 mM | >10 mM |
| CaM-M8c | 1 | T | T | T | E | 54 | 18 mM | >10 mM |
| CaM-M9c | 3 | T | D | D | E | 15 | 56 µM | >10 mM |
| CaM-M10c | 3 | D | D | T | E | 47 | 9.5 mM | >10 mM | exposed to the aqueous solvent. The addition of one equivalent of calmodulin, in the absence of metals, results in a shift of the maximum emission at 330 nm and in a 25% increase in intensity. This shows that the protein interacts with the ligand, the tryptophan of the latter then being in a more hydrophobic medium. The addition in solution of 10 equivalents of calcium gives a fluorescence emission spectrum that exhibits an increase in intensity (+20%) and the same maximum at 330 nm. These data are in agreement with a structure being obtained that is similar to the crystallographic structure of the peptide/calmodulin complex obtained in the presence of calcium (PDB 1CDL).

Figure 15:
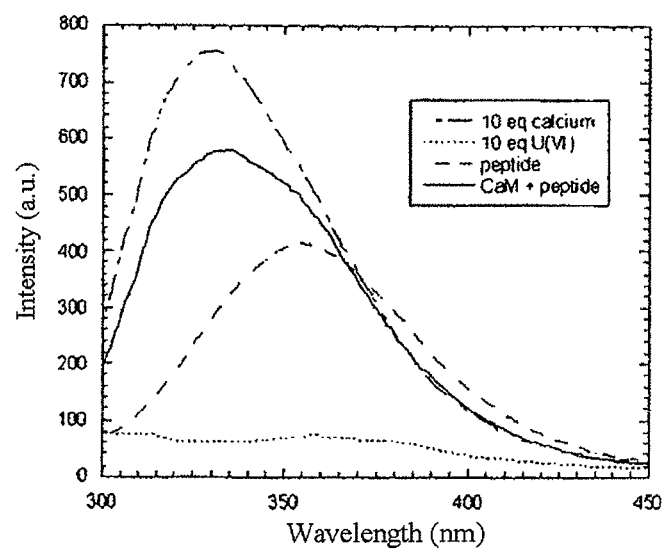
FIG. 15 illustrates the fluorescence spectra of the calmodulin ligand peptide in the absence of the protein (dashed curve), in the presence of 1 equivalent of calmodulin (continuous curve), with calcium (dashed and dotted curve) or with uranium (dotted curve)

The same experiment carried out in the presence of uranyl results in a complete extinction of the fluorescence of the ligand tryptophan (FIG. 15). This is compatible with a structure similar to that obtained in the case of calcium. In fact, the latter is a metal with a full shell, which exhibits no possible These results demonstrate that the replacement, in the complexing loop of calmodulin, of a residue D24 with a neutral residue, for example threonine, or of two residues of the residues D20, D22 and D24 with two neutral residues, for example threonine or serine, or, finally, of the three residues D20, D22 and D24 with neutral residues, for example threonine, serine or asparagine, induces a specificity for uranyl. For these mutants, the affinity for calcium ions or lanthanides is greatly reduced to the limit of detection.

As emerges from the above, the invention is in no way limited to those of its methods of implementation, execution and application which have just been described more explicitly; on the contrary, it encompasses all the variants thereof that may occur to those skilled in the art, without departing from the context of the scope of the present invention.

The invention claimed is:

1. A peptide comprising one of the sequences SEQ ID Nos. 4-7 or SEQ ID Nos. 9-12.

2. The peptide as claimed in claim 1, wherein cysteines at positions 13 and 29 of said sequences are connected via a disulfide bridge.

3. The peptide as claimed in claim 1, wherein it is conjugated to at least one fluorophore.

4. The peptide as claimed in claim 3, wherein it is conjugated to two different fluorophores.

5. The peptide as claimed in claim 3 wherein said fluorophore is a fluorescent protein selected from: EBFP, ECFP, EYFP, EGFP, DsRed, CopGFP and PhiYFP.

6. The peptide as claimed in claim 3 wherein said fluorophore is selected from dansyl, coumarin, fluorescein and Alexa derivatives.

7. The peptide as claimed in claim 1, wherein it is associated with at least one molecule that allows targeting to the kidney and/or to the bone.

8. The peptide as claimed in claim 1, wherein it is associated with a molecule that promotes its excretion in vivo.

9. A polypeptide comprising the concatenation of at least two identical or at least two different peptides as claimed in claim 1.

10. A peptide composition comprising at least one polypeptide as claimed in claim 9 and at least one suitable vehicle.

11. A fusion protein consisting of the in-frame fusion of the sequence of at least one peptide as claimed in claim 1, with the sequence of protein selected from the group consisting of calmodulin, chameleon proteins, and proteins having a helix-loop-helix type motif, capable of binding calcium.

12. The fusion protein as claimed in claim 11 wherein it is conjugated to at least one fluorophore as defined in claim 5.

13. The fusion protein as claimed in claim 12, wherein one of the ends of said protein is coupled to a fluorescence donor, and the other is coupled to a fluorescence acceptor.

14. The fusion protein as claimed in claim 13, wherein it comprises, at one of its ends, the sequence of EBFP or ECFP and, at the other end, the sequence of EGFP or of EYFP.

15. A kit for detecting a contamination with uranium comprising at least one of: a peptide as claimed in claim 1, a polypeptide derived from said peptide, a peptide composition comprising said peptide, a fusion protein derived from said peptide, an antibody that binds selectively to said peptide, or modified prokaryotic or eukaryotic cells modified with a regulatory system that includes said peptide as a regulator or repressor of a gene encoding a bioluminescent protein.

16. The fusion protein as claimed in claim 11 wherein it is conjugated to at least one fluorophore selected from the group consisting of dansyl, coumarin, fluorescein and Alexa derivatives.

\* \* \* \* \*

SEQUENCE LISTING

<160> NUMBER OF SEQ ID NOS: 24

<210> SEQ ID NO 1
<211> LENGTH: 33
<212> TYPE: PRT
<213> ORGANISM: Artificial sequence
<220> FEATURE:
<223> OTHER INFORMATION: peptide CaM

<400> SEQUENCE: 1

Glu Gln Ile Ala Glu Phe Lys Glu Ala Phe Ala Leu Phe Asp Lys Asp
1               5                   10                  15

Gly Asp Gly Thr Ile Thr Thr Lys Glu Leu Gly Thr Val Met Arg Ser
            20                  25                  30

Leu

<210> SEQ ID NO 2
<211> LENGTH: 33
<212> TYPE: PRT
<213> ORGANISM: Artificial sequence
<220> FEATURE:
<223> OTHER INFORMATION: peptide CaM-M1c

<400> SEQUENCE: 2

Glu Gln Ile Ala Glu Phe Lys Glu Ala Phe Ala Leu Cys Asp Lys Asp
1               5                   10                  15

Gly Asp Gly Tyr Ile Thr Thr Lys Glu Leu Gly Thr Cys Met Arg Ser
            20                  25                  30

Leu

<210> SEQ ID NO 3
<211> LENGTH: 33
<212> TYPE: PRT
<213> ORGANISM: Artificial sequence
<220> FEATURE:
<223> OTHER INFORMATION: peptide CaM-M2c

<400> SEQUENCE: 3

Glu Gln Ile Ala Glu Phe Lys Glu Ala Phe Ala Leu Cys Asp Lys Asp
1               5                   10                  15

Gly Asp Gly Tyr Ile Thr Thr Lys Asp Leu Gly Thr Cys Met Arg Ser
            20                  25                  30

Leu

<210> SEQ ID NO 4
<211> LENGTH: 33
<212> TYPE: PRT
<213> ORGANISM: Artificial sequence
<220> FEATURE:
<223> OTHER INFORMATION: peptide CaM-M3c

<400> SEQUENCE: 4

Glu Gln Ile Ala Glu Phe Lys Glu Ala Phe Ala Leu Cys Thr Lys Asp
1               5                   10                  15

Gly Thr Gly Tyr Ile Thr Thr Lys Glu Leu Gly Thr Cys Met Arg Ser
            20                  25                  30

Leu

<210> SEQ ID NO 5
<211> LENGTH: 33
<212> TYPE: PRT
<213> ORGANISM: Artificial sequence

```
<220> FEATURE:
<223> OTHER INFORMATION: peptide CaM-M4c

<400> SEQUENCE: 5

Glu Gln Ile Ala Glu Phe Lys Glu Ala Phe Ala Leu Cys Asn Lys Asn
1               5                   10                  15

Gly Asn Gly Tyr Ile Thr Thr Lys Glu Leu Gly Thr Cys Met Arg Ser
            20                  25                  30

Leu

<210> SEQ ID NO 6
<211> LENGTH: 33
<212> TYPE: PRT
<213> ORGANISM: Artificial sequence
<220> FEATURE:
<223> OTHER INFORMATION: peptide CaM-M5c

<400> SEQUENCE: 6

Glu Gln Ile Ala Glu Phe Lys Glu Ala Phe Ala Leu Cys Asp Lys Thr
1               5                   10                  15

Gly Thr Gly Tyr Ile Thr Thr Lys Glu Leu Gly Thr Cys Met Arg Ser
            20                  25                  30

Leu

<210> SEQ ID NO 7
<211> LENGTH: 33
<212> TYPE: PRT
<213> ORGANISM: Artificial sequence
<220> FEATURE:
<223> OTHER INFORMATION: peptide CaM-M6c

<400> SEQUENCE: 7

Glu Gln Ile Ala Glu Phe Lys Glu Ala Phe Ala Leu Cys Thr Lys Thr
1               5                   10                  15

Gly Asp Gly Tyr Ile Thr Thr Lys Glu Leu Gly Thr Cys Met Arg Ser
            20                  25                  30

Leu

<210> SEQ ID NO 8
<211> LENGTH: 17
<212> TYPE: PRT
<213> ORGANISM: Artificial sequence
<220> FEATURE:
<223> OTHER INFORMATION: peptide MLCKp

<400> SEQUENCE: 8

Arg Arg Lys Trp Gln Lys Thr Gly His Ala Val Arg Ala Ile Gly Arg
1               5                   10                  15

Leu

<210> SEQ ID NO 9
<211> LENGTH: 33
<212> TYPE: PRT
<213> ORGANISM: Artificial sequence
<220> FEATURE:
<223> OTHER INFORMATION: peptide CaM-M7c

<400> SEQUENCE: 9

Glu Gln Ile Ala Glu Phe Lys Glu Ala Phe Ala Leu Cys Ser Lys Asp
1               5                   10                  15

Gly Ser Gly Tyr Ile Thr Thr Lys Glu Leu Gly Thr Cys Met Arg Ser
            20                  25                  30
```

Leu

```
<210> SEQ ID NO 10
<211> LENGTH: 33
<212> TYPE: PRT
<213> ORGANISM: Artificial sequence
<220> FEATURE:
<223> OTHER INFORMATION: peptide CaM-M8c

<400> SEQUENCE: 10
```

Glu Gln Ile Ala Glu Phe Lys Glu Ala Phe Ala Leu Cys Thr Lys Thr
1               5                   10                  15

Gly Thr Gly Tyr Ile Thr Thr Lys Glu Leu Gly Thr Cys Met Arg Ser
            20                  25                  30

Leu

```
<210> SEQ ID NO 11
<211> LENGTH: 33
<212> TYPE: PRT
<213> ORGANISM: Artificial sequence
<220> FEATURE:
<223> OTHER INFORMATION: peptide CaM-M9c

<400> SEQUENCE: 11
```

Glu Gln Ile Ala Glu Phe Lys Glu Ala Phe Ala Leu Cys Thr Lys Asp
1               5                   10                  15

Gly Asp Gly Tyr Ile Thr Thr Lys Glu Leu Gly Thr Cys Met Arg Ser
            20                  25                  30

Leu

```
<210> SEQ ID NO 12
<211> LENGTH: 33
<212> TYPE: PRT
<213> ORGANISM: Artificial sequence
<220> FEATURE:
<223> OTHER INFORMATION: peptide CaM-M10c

<400> SEQUENCE: 12
```

Glu Gln Ile Ala Glu Phe Lys Glu Ala Phe Ala Leu Cys Asp Lys Asp
1               5                   10                  15

Gly Thr Gly Tyr Ile Thr Thr Lys Glu Leu Gly Thr Cys Met Arg Ser
            20                  25                  30

Leu

```
<210> SEQ ID NO 13
<211> LENGTH: 12
<212> TYPE: PRT
<213> ORGANISM: artificial sequence
<220> FEATURE:
<223> OTHER INFORMATION: CaM peptide 20-31

<400> SEQUENCE: 13
```

Asp Lys Asp Gly Asp Gly Thr Ile Thr Thr Lys Glu
1               5                   10

```
<210> SEQ ID NO 14
<211> LENGTH: 12
<212> TYPE: PRT
<213> ORGANISM: artificial sequence
<220> FEATURE:
<223> OTHER INFORMATION: CaM peptide 56-67

<400> SEQUENCE: 14
```

```
Asp Ala Asp Gly Asn Gly Thr Ile Asp Phe Pro Glu
1               5                   10
```

<210> SEQ ID NO 15
<211> LENGTH: 12
<212> TYPE: PRT
<213> ORGANISM: artificial sequence
<220> FEATURE:
<223> OTHER INFORMATION: CaM peptide 93-104

<400> SEQUENCE: 15

```
Asp Lys Asp Gly Asn Gly Tyr Ile Ser Ala Ala Glu
1               5                   10
```

<210> SEQ ID NO 16
<211> LENGTH: 12
<212> TYPE: PRT
<213> ORGANISM: artificial sequence
<220> FEATURE:
<223> OTHER INFORMATION: CaM peptide 129-140

<400> SEQUENCE: 16

```
Asp Ile Asp Gly Asp Gly Gln Val Asn Tyr Glu Glu
1               5                   10
```

<210> SEQ ID NO 17
<211> LENGTH: 13
<212> TYPE: PRT
<213> ORGANISM: artificial sequence
<220> FEATURE:
<223> OTHER INFORMATION: CaM peptide 7-19

<400> SEQUENCE: 17

```
Glu Gln Ile Ala Glu Phe Lys Glu Ala Phe Ser Leu Phe
1               5                   10
```

<210> SEQ ID NO 18
<211> LENGTH: 7
<212> TYPE: PRT
<213> ORGANISM: artificial sequence
<220> FEATURE:
<223> OTHER INFORMATION: CaM peptide 32-38

<400> SEQUENCE: 18

```
Leu Gly Thr Val Met Arg Ser
1               5
```

<210> SEQ ID NO 19
<211> LENGTH: 11
<212> TYPE: PRT
<213> ORGANISM: artificial sequence
<220> FEATURE:
<223> OTHER INFORMATION: CaM peptide 45-55

<400> SEQUENCE: 19

```
Glu Ala Glu Leu Gln Asp Met Ile Asn Glu Val
1               5                   10
```

<210> SEQ ID NO 20
<211> LENGTH: 11
<212> TYPE: PRT
<213> ORGANISM: artificial sequence
<220> FEATURE:
<223> OTHER INFORMATION: CaM peptide 68-78

<400> SEQUENCE: 20

```
Phe Leu Thr Met Met Ala Arg Lys Met Lys Asp
1               5                   10

<210> SEQ ID NO 21
<211> LENGTH: 14
<212> TYPE: PRT
<213> ORGANISM: artificial sequence
<220> FEATURE:
<223> OTHER INFORMATION: CaM peptide 79-92

<400> SEQUENCE: 21

Thr Asp Ser Glu Glu Ile Arg Glu Ala Phe Arg Val Phe
1               5                   10

<210> SEQ ID NO 22
<211> LENGTH: 7
<212> TYPE: PRT
<213> ORGANISM: artificial sequence
<220> FEATURE:
<223> OTHER INFORMATION: CaM peptide 105-111

<400> SEQUENCE: 22

Leu Arg His Val Met Thr Asn
1               5

<210> SEQ ID NO 23
<211> LENGTH: 11
<212> TYPE: PRT
<213> ORGANISM: artificial sequence
<220> FEATURE:
<223> OTHER INFORMATION: CaM peptide 118-128

<400> SEQUENCE: 23

Asp Glu Glu Val Asp Glu Met Ile Arg Glu Ala
1               5                   10

<210> SEQ ID NO 24
<211> LENGTH: 7
<212> TYPE: PRT
<213> ORGANISM: artificial sequence
<220> FEATURE:
<223> OTHER INFORMATION: CaM peptide 141-147

<400> SEQUENCE: 24

Phe Val Gln Met Met Thr Ala
1               5
```